(12) United States Patent
Coleman et al.

(10) Patent No.: US 6,926,731 B2
(45) Date of Patent: Aug. 9, 2005

(54) SURGICAL STAPLER

(76) Inventors: James Coleman, 20 Greenmount Road, Terenure (IE), Dublin 6; Christy Cummins, 54 Knockowen, Tullamore (IE); Chris Martin, 33 Greentrees Ave., Dublin 12 (IE); Thomas Anthony, 49 Grange Downs, Rathfarnham (IE), Dublin 14; Sean Morris, Kiltoom, Athlone (IE)

( * ) Notice: Subject to any disclaimer, the term of this patent is extended or adjusted under 35 U.S.C. 154(b) by 9 days.

(21) Appl. No.: 10/455,768

(22) Filed: Jun. 4, 2003

(65) Prior Publication Data

US 2003/0199924 A1 Oct. 23, 2003

Related U.S. Application Data

(63) Continuation of application No. 09/948,813, filed on Sep. 7, 2001, now Pat. No. 6,582,452.

(30) Foreign Application Priority Data

Sep. 8, 2000 (IE) .......................................... S2000-0724
Sep. 8, 2000 (IE) .......................................... S2000-0722

(51) Int. Cl.[7] ............................................... A61B 17/04
(52) U.S. Cl. ...................... 606/213; 606/216; 227/175.1
(58) Field of Search ......................................... 606/213

(56) References Cited

U.S. PATENT DOCUMENTS

| 3,482,428 A | 12/1969 | Kapitanov et al. |
| 4,014,492 A | 3/1977 | Rothfuss |
| 4,724,840 A | 2/1988 | McVay et al. |
| 4,771,782 A | 9/1988 | Millar |
| 4,832,688 A | 5/1989 | Sagae |
| 4,836,204 A | 6/1989 | Landymore |
| 5,108,421 A | 4/1992 | Fowler |
| 5,147,381 A | 9/1992 | Heimerl et al. |

(Continued)

FOREIGN PATENT DOCUMENTS

| EP | 0 386 361 | 9/1990 |
| EP | 0 534 696 | 3/1993 |
| EP | 0 756 851 | 2/1997 |
| EP | 0 774 237 | 5/1997 |
| EP | 0 941 697 | 9/1999 |
| FR | 2 443 238 | 7/1980 |
| GB | 1 358 466 | 7/1974 |
| WO | WO 97/20505 | 6/1997 |
| WO | WO 98/25508 | 6/1998 |
| WO | WO 0007640 | * 2/2000 |

*Primary Examiner*—Gary Jackson
(74) *Attorney, Agent, or Firm*—Nutter, McClennen & Fish LLP

(57) ABSTRACT

A surgical stapler comprises a hollow shaft 10 and a tube 92 slidable axially within the shaft between a forward position wherein one end 96 of the tube projects beyond a free end of the shaft to enter a puncture site in a blood vessel and a rearward position wherein the end of the locator tube is retracted within the shaft. A surgical staple 40 straddles the tube 92 and is slidable thereon forwardly towards an anvil 24 against which the staple may be deformed to staple together the opposite edges of the puncture site. A cam mechanism drives the staple forwardly along the tube 92 into deforming engagement with the anvil and at the same time retracts the tube into the shaft in time to allow the legs of the staple to close onto the puncture site.

43 Claims, 19 Drawing Sheets

U.S. PATENT DOCUMENTS

| | | |
|---|---|---|
| 5,192,300 A | 3/1993 | Fowler |
| 5,275,616 A | 1/1994 | Fowler |
| 5,292,309 A | 3/1994 | Van Tassel et al. |
| 5,292,332 A | 3/1994 | Lee |
| 5,304,184 A | 4/1994 | Hathaway |
| 5,395,030 A | 3/1995 | Kuramoto et al. |
| 5,413,571 A | 5/1995 | Katsaros |
| 5,431,639 A | 7/1995 | Shaw |
| 5,443,481 A | 8/1995 | Lee |
| 5,470,010 A | 11/1995 | Rothfuss et al. |
| 5,478,352 A | 12/1995 | Fowler |
| 5,527,322 A | 6/1996 | Klein et al. |
| 5,536,251 A | 7/1996 | Evard et al. |
| 5,560,532 A | 10/1996 | DeFonzo et al. |
| 5,591,205 A | 1/1997 | Fowler |
| 5,601,602 A | 2/1997 | Fowler |
| 5,620,461 A | 4/1997 | Muijs Van De Moer |
| 5,643,318 A | 7/1997 | Tsukernik et al. |
| 5,645,566 A | 7/1997 | Brenneman |
| 5,674,231 A | 10/1997 | Green et al. |
| 5,676,689 A | 10/1997 | Kensey et al. |
| 5,695,504 A | 12/1997 | Gifford |
| 5,716,375 A | 2/1998 | Fowler |
| 5,810,846 A | 9/1998 | Virnich et al. |
| 5,855,312 A | 1/1999 | Toledano |
| 5,861,005 A | 1/1999 | Kontos |
| 6,004,341 A | 12/1999 | Zhu |
| 6,007,563 A | 12/1999 | Nash et al. |
| 6,022,372 A | 2/2000 | Kontos |
| 6,048,358 A | 4/2000 | Barak |
| 6,056,768 A | 5/2000 | Cates |
| 6,090,130 A | 7/2000 | Nash et al. |
| 6,197,042 B1 * | 3/2001 | Ginn et al. ............... 606/213 |
| 6,277,140 B2 * | 8/2001 | Ginn et al. ............... 606/213 |
| 6,322,580 B1 * | 11/2001 | Kanner ...................... 606/213 |
| 6,348,064 B1 | 2/2002 | Kanner |
| 6,461,364 B1 * | 10/2002 | Ginn et al. ............... 606/142 |
| 6,506,210 B1 * | 1/2003 | Kanner ...................... 606/213 |
| 6,533,762 B2 | 3/2003 | Kanner et al. |
| 6,623,510 B2 | 9/2003 | Carley et al. |
| 6,632,238 B2 * | 10/2003 | Ginn et al. ............... 606/213 |
| 6,679,904 B2 * | 1/2004 | Gleeson et al. ............ 606/219 |
| 6,719,777 B2 | 4/2004 | Ginn et al. |
| 6,755,842 B2 | 6/2004 | Kanner et al. |
| 6,767,356 B2 | 7/2004 | Kanner et al. |
| 2001/0007077 A1 * | 7/2001 | Ginn et al. ............... 606/213 |
| 2002/0107542 A1 * | 8/2002 | Kanner et al. ............ 606/213 |
| 2002/0151921 A1 | 10/2002 | Kanner et al. |
| 2003/0004543 A1 * | 1/2003 | Gleeson et al. |
| 2003/0097140 A1 | 5/2003 | Kanner |
| 2003/0109890 A1 | 6/2003 | Kanner et al. |
| 2004/0010285 A1 | 1/2004 | Carley et al. |
| 2004/0254591 A1 | 12/2004 | Kanner et al. |
| 2004/0267312 A1 | 12/2004 | Kanner et al. |

\* cited by examiner

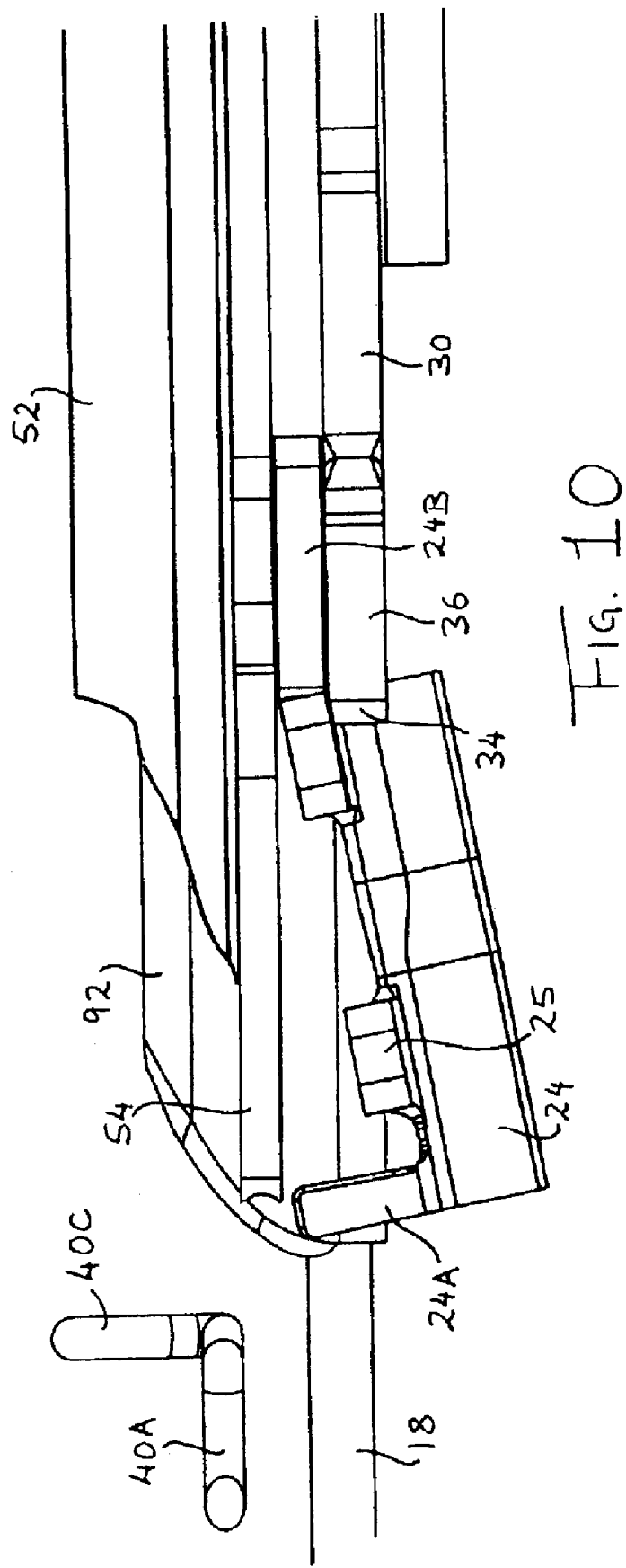

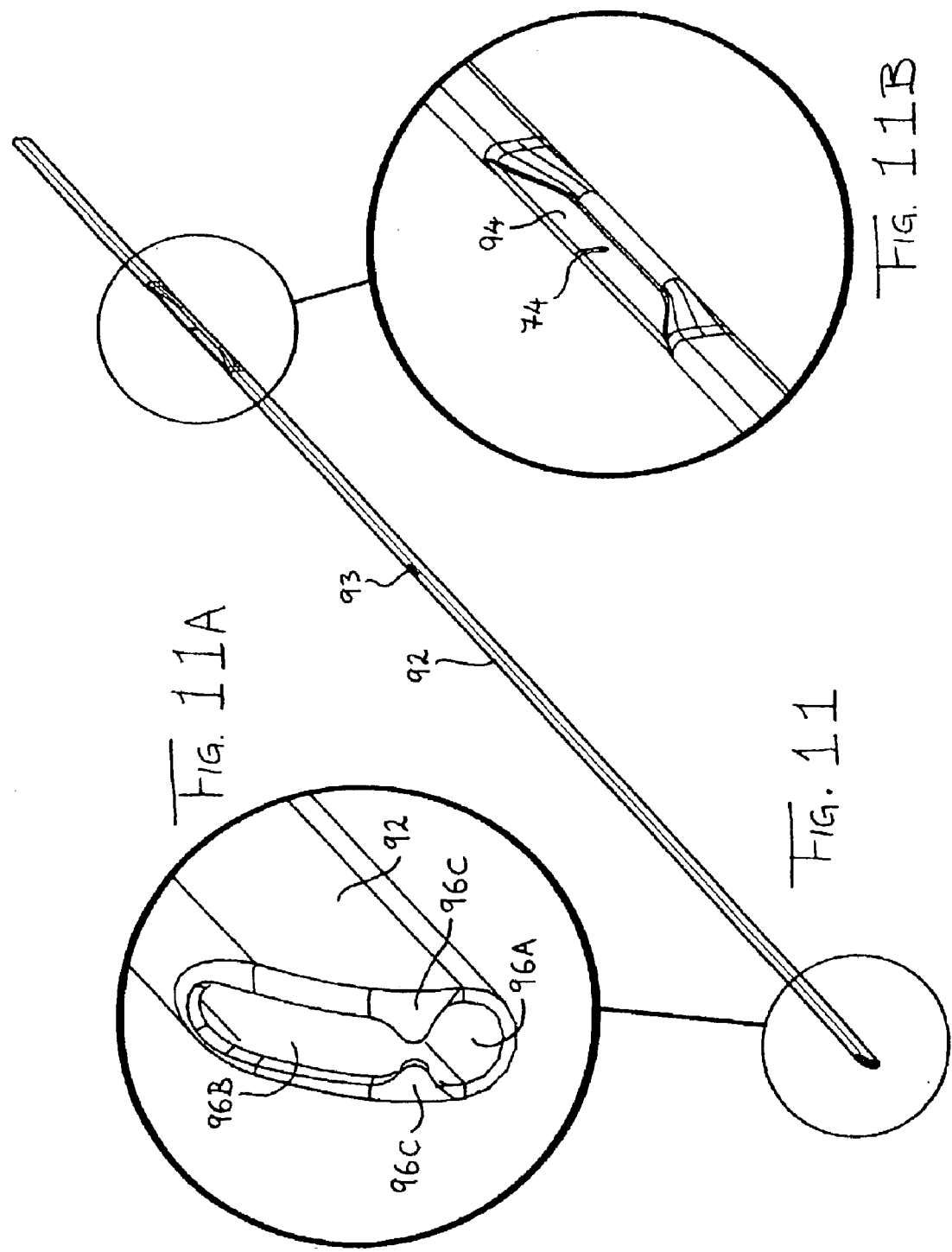

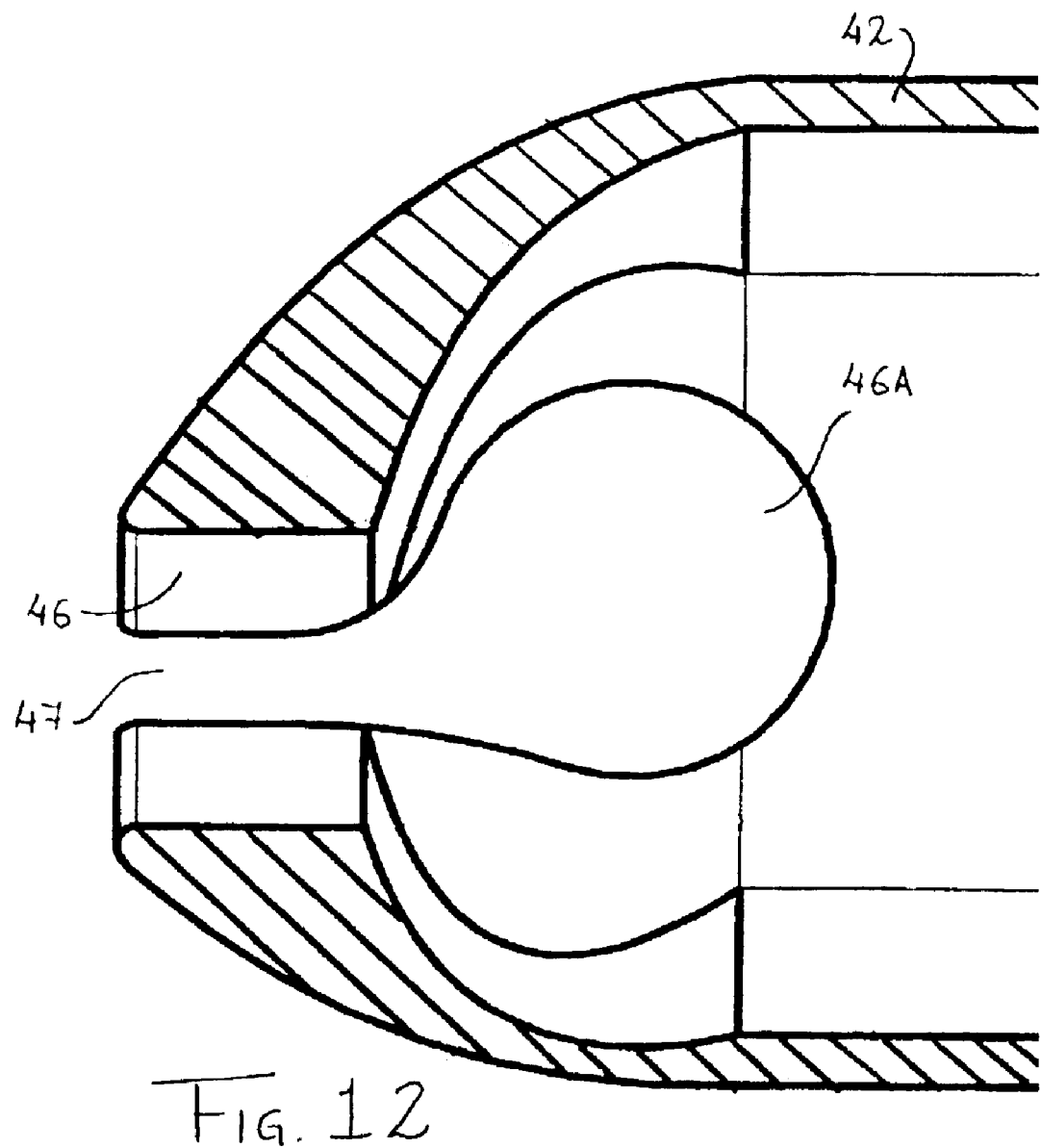

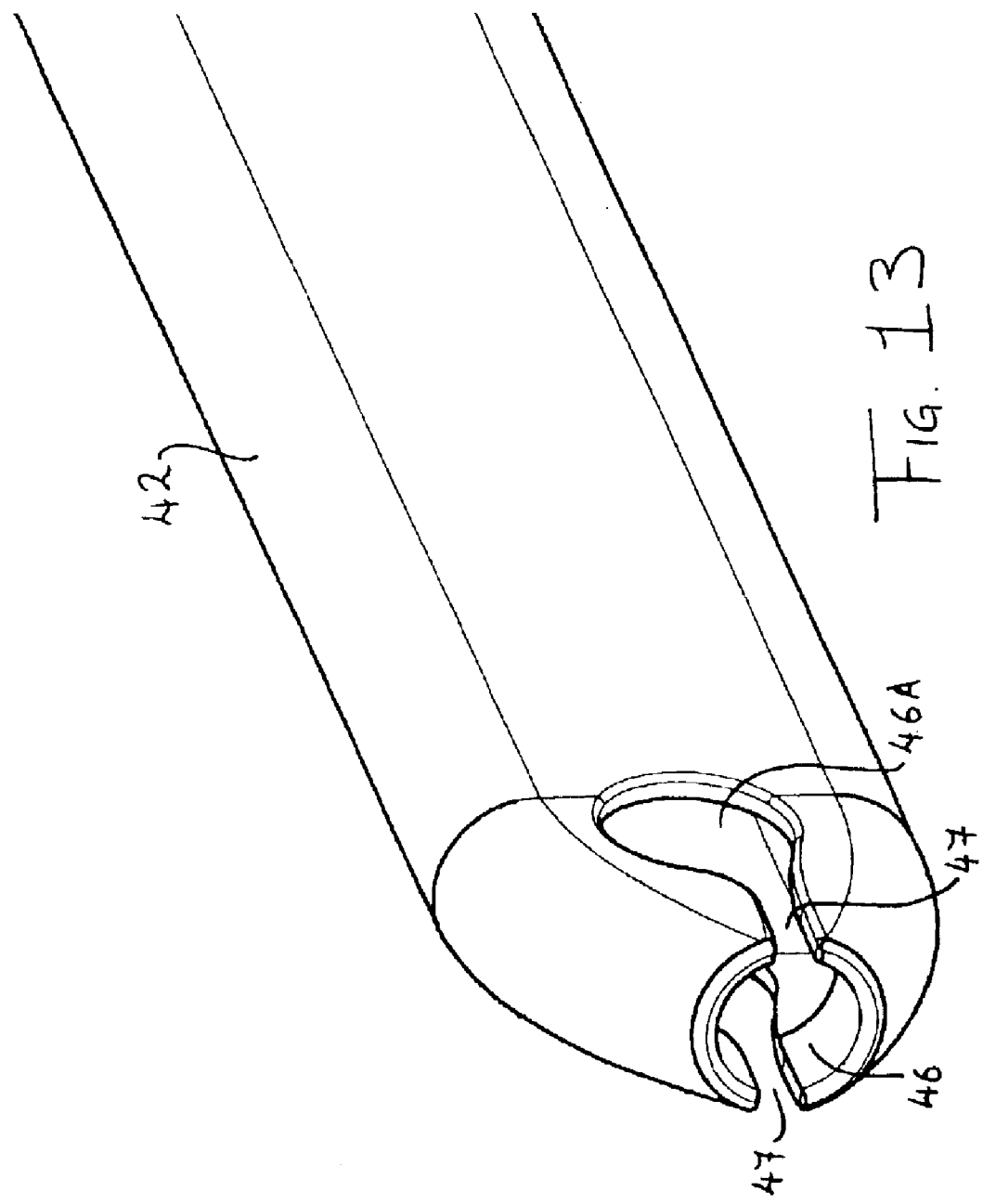

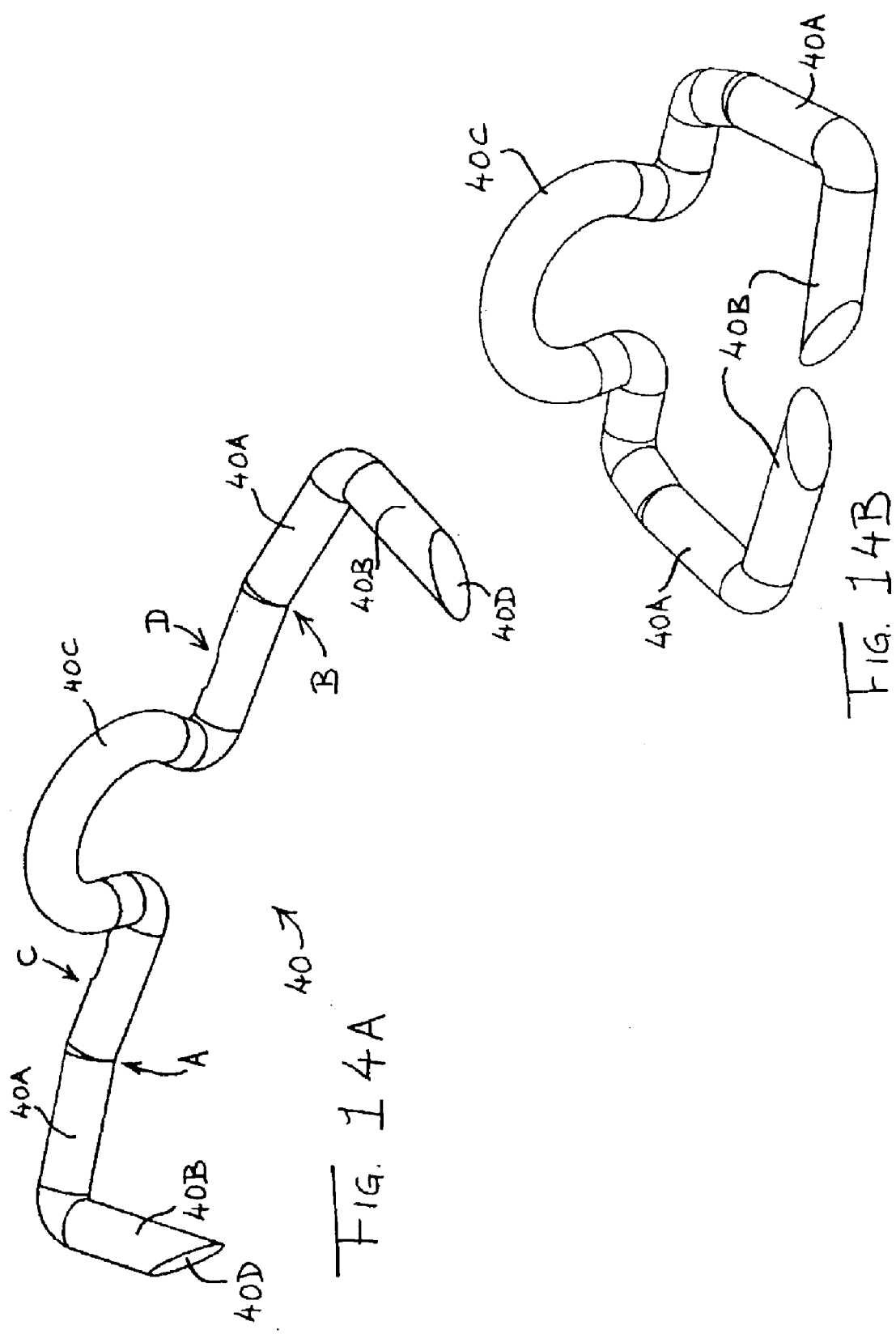

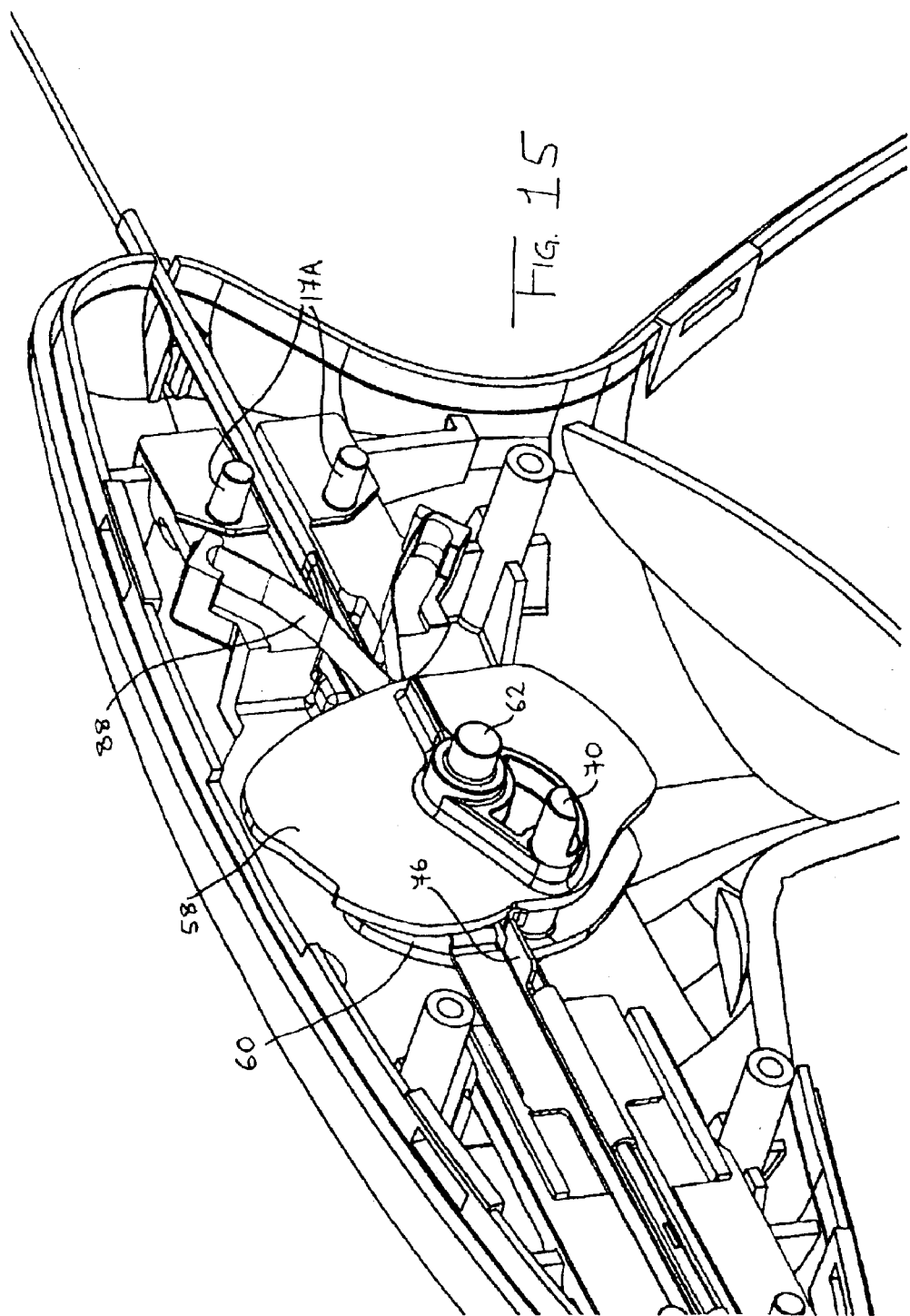

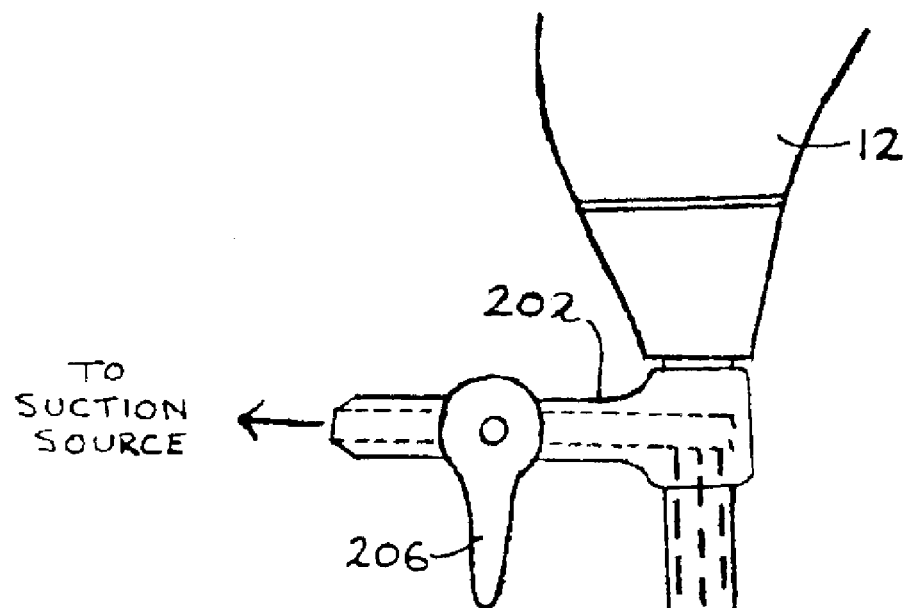
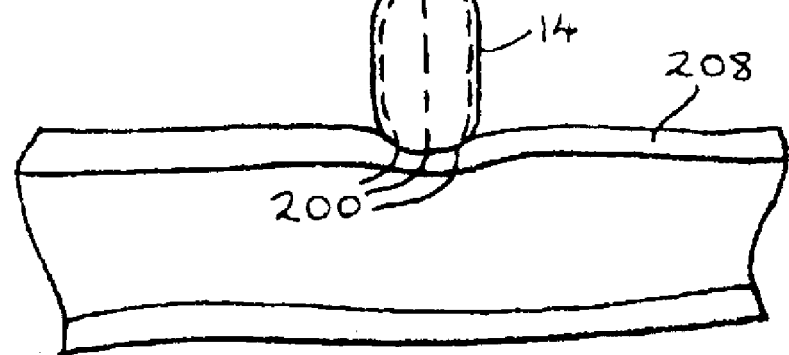
Fig. 17

SURGICAL STAPLER

CROSS-REFERENCE TO RELATED APPLICATIONS

This application is a continuation of application Ser. No. 09/948,813, filed Sep. 7, 2001, now U.S. Pat. No. 6,582,452, entitled "Surgical Stapler," which claims priority to Ireland Application No. S2000/0722, filed Sep. 8, 2000 and Ireland Application No. S2000/0724, filed Sep. 8, 2000, each of which are hereby incorporated by reference in their entirety.

FIELD OF THE INVENTION

The present invention relates to an instrument, herein called a surgical stapler, for closing a puncture in a liquid-carrying vessel by applying a staple across the puncture so as to effect a closure. The invention relates particularly to surgical staplers for closing punctures in blood vessels.

BACKGROUND TO THE INVENTION

When performing catheterisation procedures, such as angiography or angioplasty, a catheter is generally introduced into the vascular system by first penetrating the skin, underlying tissues and blood vessel with a sharpened hollow needle. Next, a guidewire is commonly inserted through the lumen of the hollow needle and is caused to enter the selected blood vessel. Subsequently the needle is typically stripped off the guidewire and a combination of a dilator and/or introducer (or an introducer alone) are fed over the guidewire and pushed through the skin to enter the blood vessel. The guidewire can then be removed and a desired catheter to carry out the procedure is fed through the lumen of the introducer and advanced through the vascular system until the working end of the catheter is appropriately positioned. Following the conclusion of the catheterisation procedure the working catheter will be withdrawn and subsequently the dilator and/or introducer will also be removed from the wound. Following this procedure the vessel puncture must be closed in order to prevent loss of blood through the puncture hole.

Typically the wound is closed by maintaining external pressure over the vessel until the puncture naturally seals. This procedure can take approximately 30 minutes with the length of time usually being greater if the patient is hypertensive or anticoagulated. The procedure can also be uncomfortable for the patient and involves costly professional time on the part of the hospital staff. Other pressure techniques such as pressure bandages, sandbags or clamps have been employed but these also involve ensuring the patient remains motionless for an extended period of time and is monitored to ensure the effectiveness of the procedure.

A number of devices have been developed in recent times which provide an obstruction in the area of the puncture in order to prevent bleeding. For example, U.S. Pat. Nos. 4,852,568 and 4,890,612 disclose a device which utilises a collagen plug which when placed at the blood vessel opening absorbs body fluids, swells and affects a seal. Other plug like devices, for example U.S. Pat. No. 5,222,974 and U.S. Pat. No. 5,282,827, describe a plug and anchor device, the anchor being positioned inside the vessel and the collagen plug outside the vessel thereby sandwiching the puncture between both and effecting a closure.

WO 98/17179 discloses a surgical stapler having a blood locator tube adjacent the stapling head. A guidewire passes through an opening at the end of the tube and up through a hollow bore in the tube, so that the stapler can be fed onto the guidewire and down onto the puncture site. When the device reaches the puncture site, the tip of the tube enters the blood flow within the artery and blood passes through the tube and out of the distal end at a point visible to the clinician. The clinician can then actuate the stapling mechanism in the knowledge that the stapling head is at the puncture site in the arterial wall.

It is an object of the present invention to provide an instrument for closing a puncture in a liquid-carrying vessel by stapling.

SUMMARY OF THE INVENTION

According to the present invention there is provided a surgical stapler comprising a shaft, a locator slidable axially of the shaft between a forward position wherein the locator projects beyond a free end of the shaft to enter a puncture site in a liquid-carrying vessel in a human or animal, thereby to locate the free end of the shaft at the puncture site, and a rearward position wherein the locator is retracted relative to the shaft, a surgical staple straddling the locator and slidable forwardly thereon, said staple having forwardly pointing legs disposed respectively on opposite sides of the locator, an anvil against which the staple may be deformed to staple together opposite edges of the puncture site, and an actuator for driving the staple forwardly along the locator into deforming engagement with the anvil and for retracting the locator in coordination with the movement of the staple such that the locator is withdrawn from between the legs of the staple in time to allow the legs of the staple to staple together opposite edges of the puncture site.

In another aspect the invention provides a method of stapling closed a puncture site in a liquid-carrying vessel in a human or animal body, comprising the steps of:

introducing a stapling mechanism to the location of the vessel;

positioning the stapling mechanism at the puncture site by means of a locator associated with the stapling mechanism and projecting forwardly thereof, the locator sensing the position of the puncture site by entering the vessel at the site;

delivering a staple to, and deforming the staple to close, the puncture site; and in co-ordination with the delivery and deformation of the staple, withdrawing the locator from the puncture site such that the locator is fully withdrawn from the vessel by the time the staple is fully deformed to close the puncture site.

Preferably, the steps of delivering and deforming the staple and in co-ordination therewith withdrawing the locator are effected by operating a single control on a stapler actuating mechanism.

BRIEF DESCRIPTION OF THE DRAWINGS

An embodiment of the invention will now be described, by way of example, with reference to the accompanying drawings, in which:

FIG. 1(A) is an enlarged perspective view of the free end of the shaft of the stapler of FIG. 1;

FIG. 10 is a side elevation of the components of FIG. 9 in the post-fire position;

FIG. 11 is a perspective view of the blood locator tube with enlarged views of the front and rear portions, FIG. 11A and FIG. 11B respectively;

FIG. 12 is a side sectional elevation of the front portion of an alternative embodiment of the blood locator tube of the stapler;

FIG. 13 is a perspective view of the front portion of the blood locator tube shown in FIG. 12;

FIG. 14(A) is a perspective view of the surgical staple in the pre-fire (pre-deformed) state;

FIG. 14(B) is a perspective view of the surgical staple in the post-fire (deformed) state;

FIG. 15 is an enlarged perspective view of the cam mechanism;

FIG. 17 is a side elevation of the shaft section of the device and suction port.

DETAILED DESCRIPTION OF THE PREFERRED EMBODIMENTS

Figure 2:
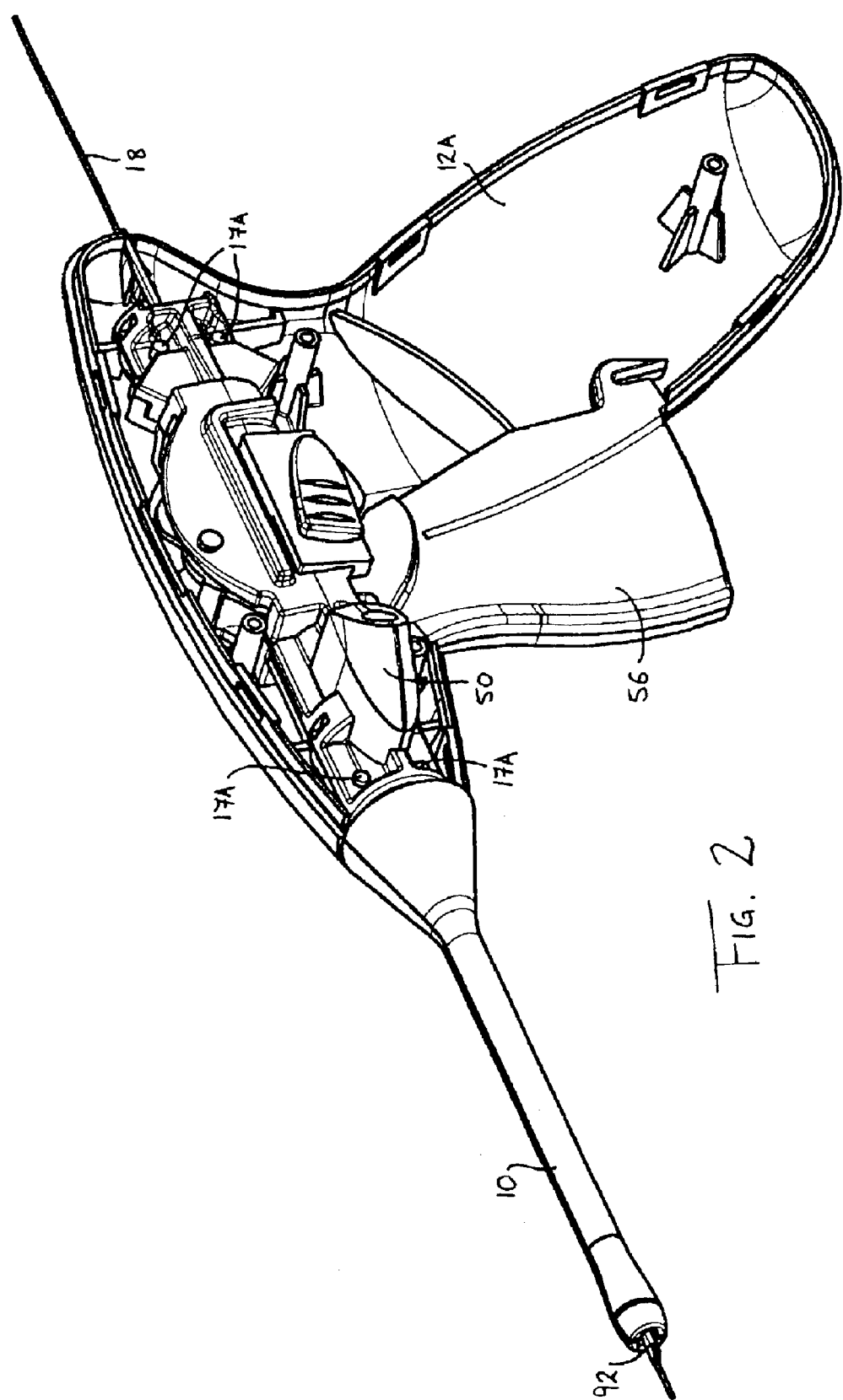
FIG. 2 is a perspective view of the stapler of FIG. 1 with the left-hand side handle removed.
Figure 4:
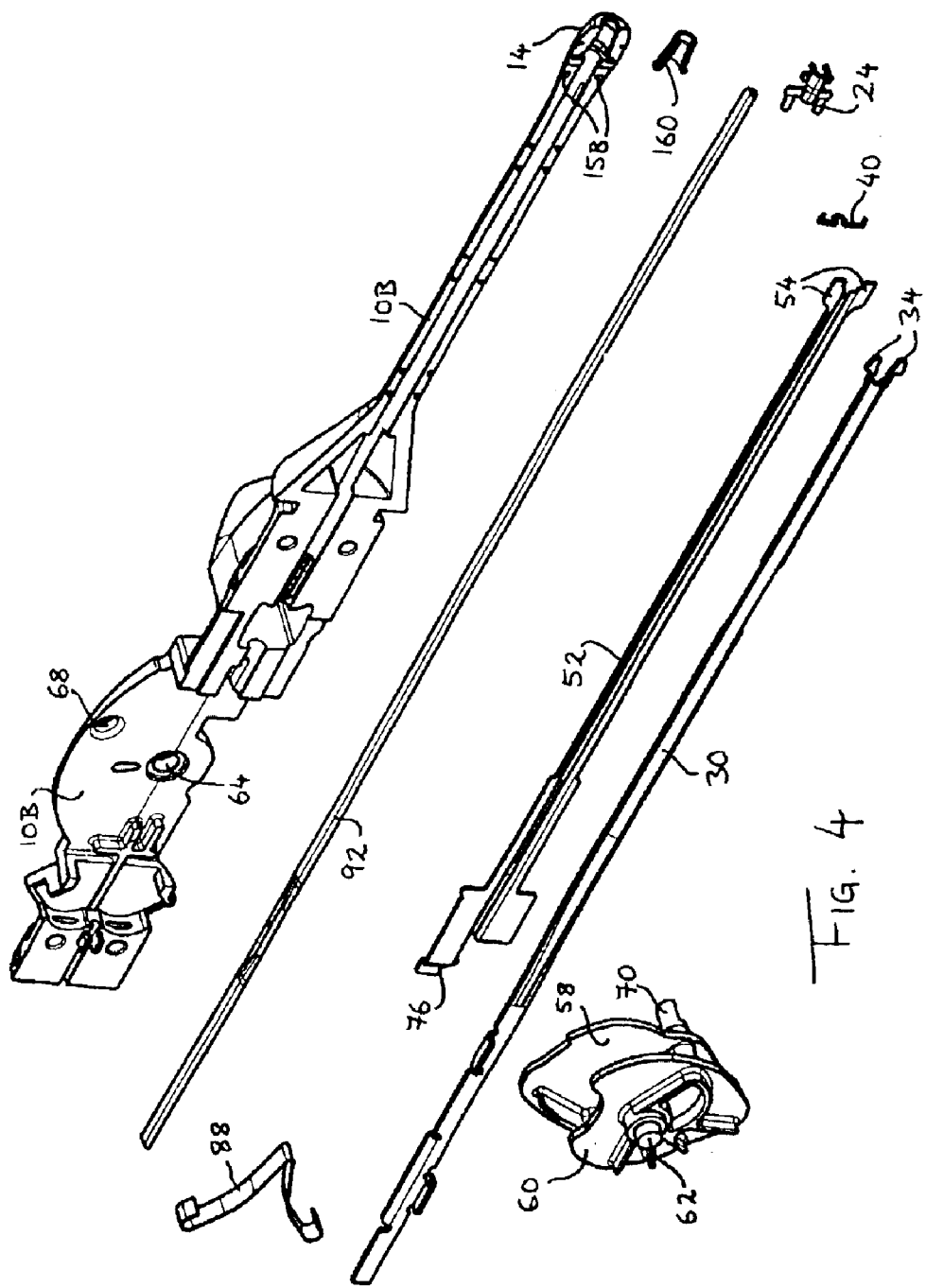
FIG. 4 is an exploded perspective view of the components seen in FIG. 3 further omitting the left-hand side handle.
Figure 5:
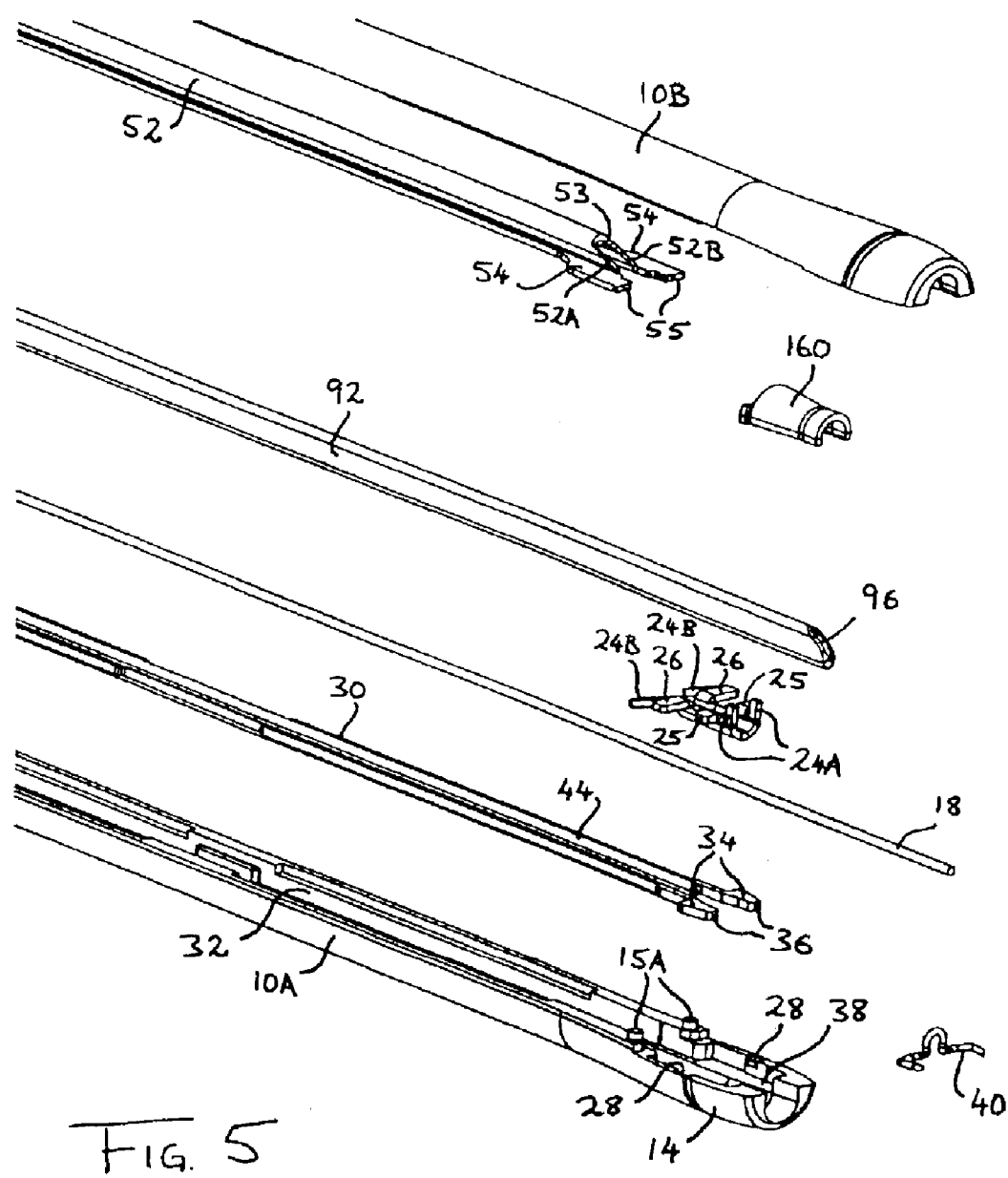
FIG. 5 is an exploded perspective view of the internal components at the free end of the shaft.

Referring to the drawings, the stapler comprises a rigid shaft 10 extending from a moulded plastic housing 12 shaped in the form of a pistol-like handle. The shaft 10, which is hollow to accommodate various moving components to be described, comprises right and lefthand sides 10A, 10B respectively which are secured together at the distal free end by a section of heat shrinkable tubing 91 in combination with interference pins and mating cavities 15A and 15B (FIGS. 4 and 5) along the edges of the distal tip, and at the proximal end by pins 17A mating in an interference fit with corresponding cavities 17B (FIGS. 2 and 3) captured within the housing 12. Likewise, the housing 12 comprises left and right-hand sides 12A, 12B respectively.

The major part of the exposed length of the shaft 10 has a constant circular cross-section, but at its free end the shaft 10 has a portion 14 of increased diameter having a "bullet" profile. One end of this bullet portion 14 is tapered down toward a staple exit slot 16 while the other end is tapered down to the remaining section of the shaft, which extends back into the housing 12. The ratio of the maximum diameter of the bullet portion 14 to the diameter of the remaining section of exposed shaft is approximately 5:4. Heat shrink sleeve 91 sits flush with the surface of the bullet portion 14, to ensure atraumatic entry, percutaneously, into the tissue.

The reason for the bullet profile is so that the shaft 10 is as atraumatic as possible during introduction to the body to minimise the amount of force and tissue dilation required when tracking the device percutaneously over a guidewire 18 and onto the surface of a blood vessel adjacent a puncture hole, as will be described. In an alternative embodiment, not shown, the bullet portion 14 is oval in cross-section with the major axis of the oval being coincident with the staple exit slot 16, so as to minimise the circumferential length for a given staple width.

The bullet portion 14 of the shaft 10 houses a staple 40 and a staple delivery mechanism (FIGS. 4 to 7). The staple delivery mechanism comprises a tiltable anvil 24 and a pair of rod-like actuating members, namely an elongated anvil support 30 and an elongated staple former 52, the latter being slidable in the shaft 10 and operated by a trigger-operated cam mechanism 62 in the handle housing 12.

The anvil 24 has a pair of upstanding fingers 24A at the front and a pair of downwardly inclined tilt arms 24B at the rear. The anvil 24 is tiltably mounted in the bullet portion 14 by a pair of wings 26 which are pivotable in recesses 28 in the right-hand side 10A of the shaft 10 (the wings 26 are retained in the recesses by the underside of projections 54 on the former 52).

Figure 6:
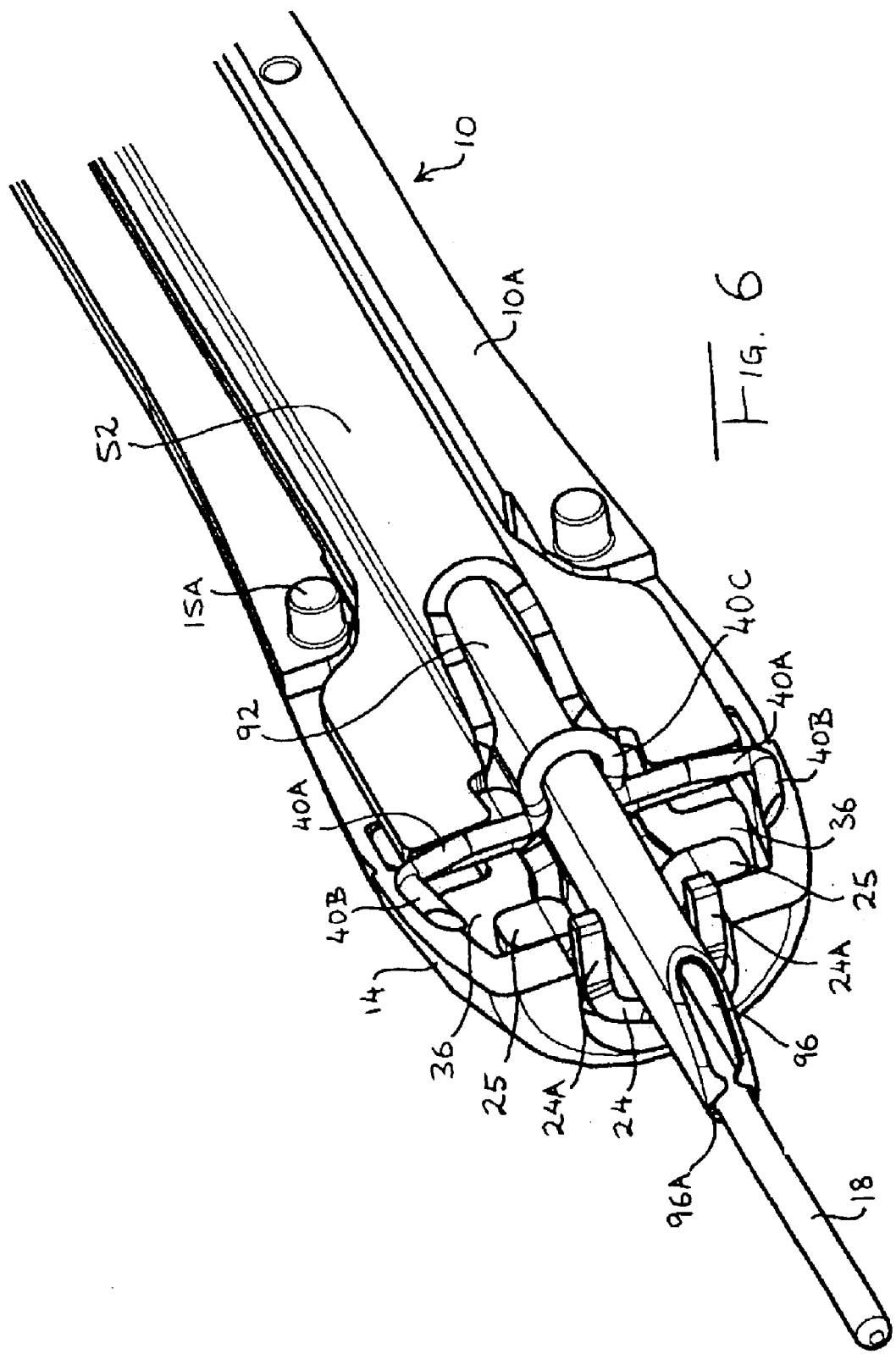
FIG. 6 is a perspective view of the internal components at the free end of the shaft in the pre-fire position and omitting the left-hand side of the shaft.
Figure 7:
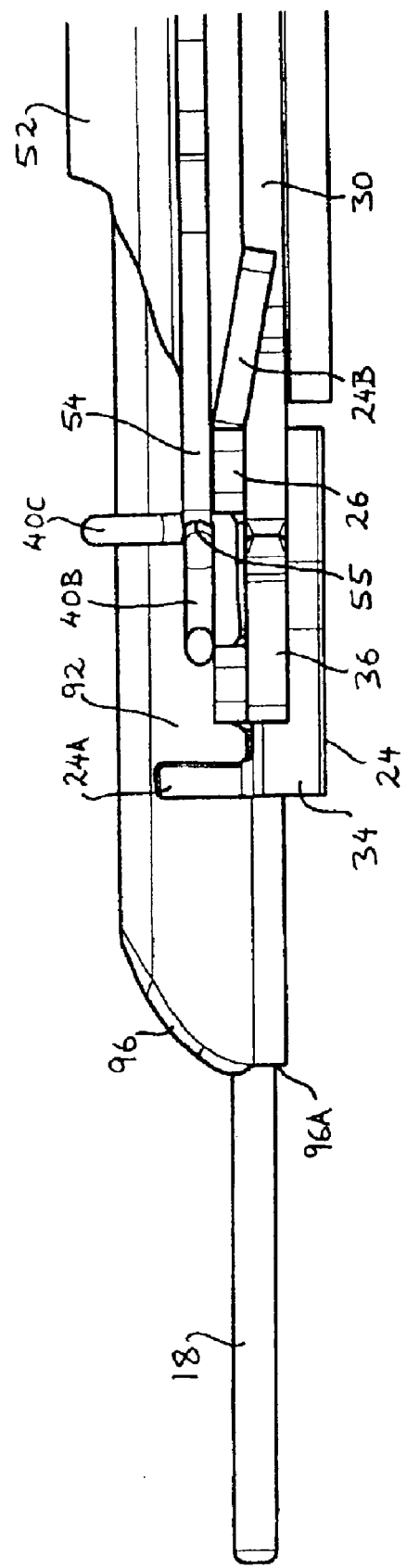
FIG. 7 is a side elevation of the components of FIG. 6 in the pre-fire position.

Tilting of the anvil 24 is effected by the cam mechanism 62 via the anvil support 30, which is slidable axially within the right-hand shaft side 10A in channel 32. The front end of the anvil support 30 is bifurcated to form two arms 34 having lateral projections 36 (FIGS. 6 and 7). The arms slide in rebates 38 in the right-hand shaft side 10A. The anvil support 30 is movable, by the cam mechanism 62, from a forward position, FIGS. 6 and 7, wherein the arms 34 extend under the anvil's support wings 25 to support the anvil forming fingers 24A directly in front of a surgical staple 40 to be delivered, to a rearward position, FIG. 10, wherein the arms 34 are withdrawn under the downwardly inclined tilt arms 24B at the rear of the anvil 24 so as to tilt the anvil anti-clockwise (as seen in FIG. 10) and displace the fingers 24A out of the path of the staple 40. The angle of incline of tilt arms 24B may be increased to cause separation of the two shaft halves, in addition to displacing the fingers 24A out of the path of the formed staple, to aid in staple release. This is achieved by the anvil (in its fully tilted position) applying pressure to the underside of former 52 and the upper surface of the right shaft 10A.

Referring additionally to FIGS. 11, 11A and 11B, a hollow blood locator tube 92 is slidable axially within the shaft 10 in a channel 44 in the anvil support 30 and in an opposing U-shaped channel 53 in the staple former 52. The tube 92 extends the full length of the shaft 10 and has a constant, generally oval or elongated cross-section, except at its distal tip 14 where the locator tube 92 is formed into a narrow opening 96 and at a crimped region 94 towards the rear of the tube 92 which is formed to allow only the guidewire 18 and not blood to exit the rear of the locator tube.

Figure 9:
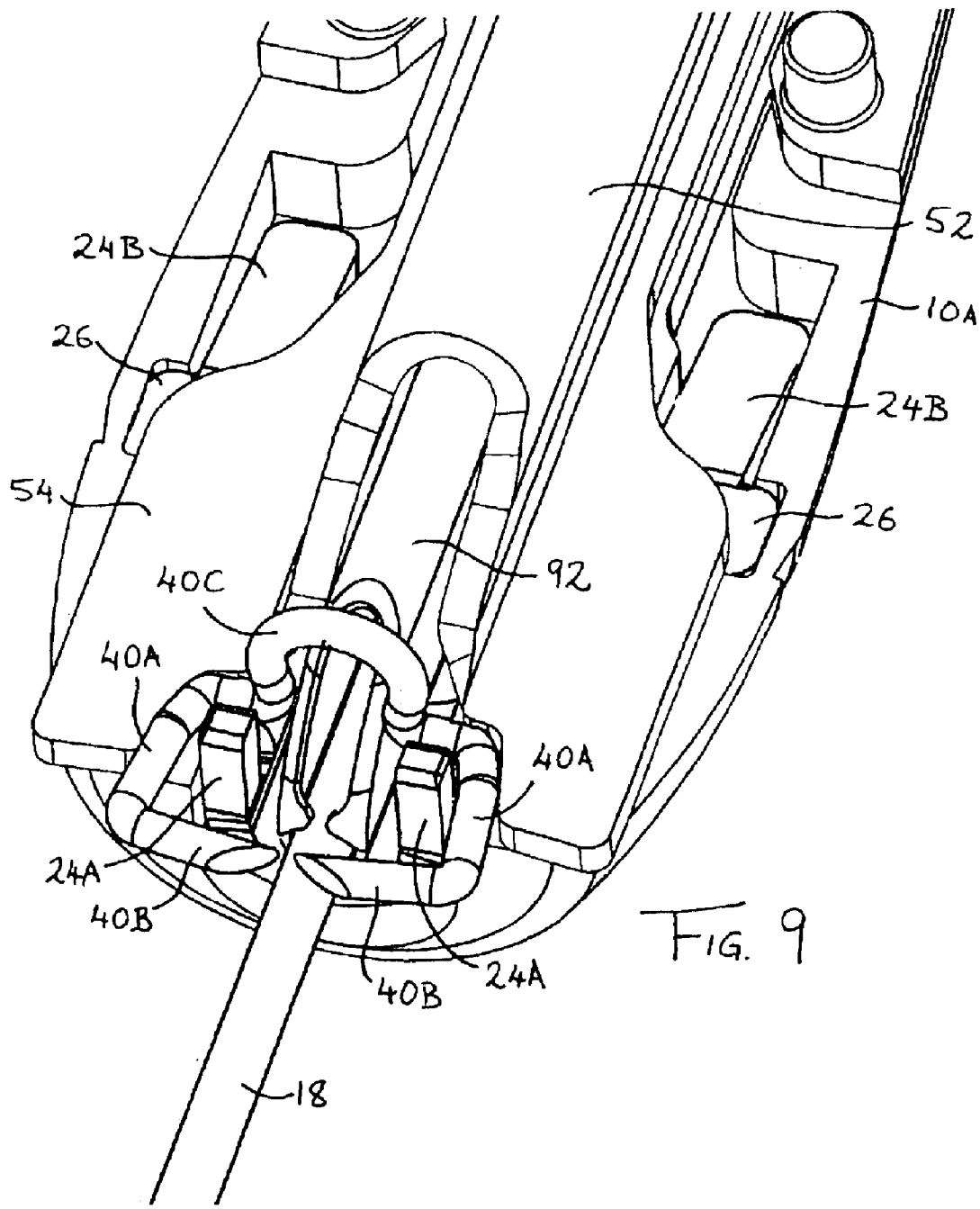
FIG. 9 is a perspective view of the internal components of the free end, showing the position of the components in mid-cycle with fully formed staple.

Under the action of the cam mechanism 62 the tube 92 is slidable axially in the shaft 10 between a forward position, FIGS. 6 and 7, wherein its front end projects beyond the bullet portion 14 of the shaft 10 under the influence of a leaf spring 88 to be described, and a rearward position, FIGS. 9 and 10, wherein the front end of the tube 92 is retracted within the bullet portion 14 behind the fingers 24A of the anvil 24 during the rotation of cam 62.

Figure 1:
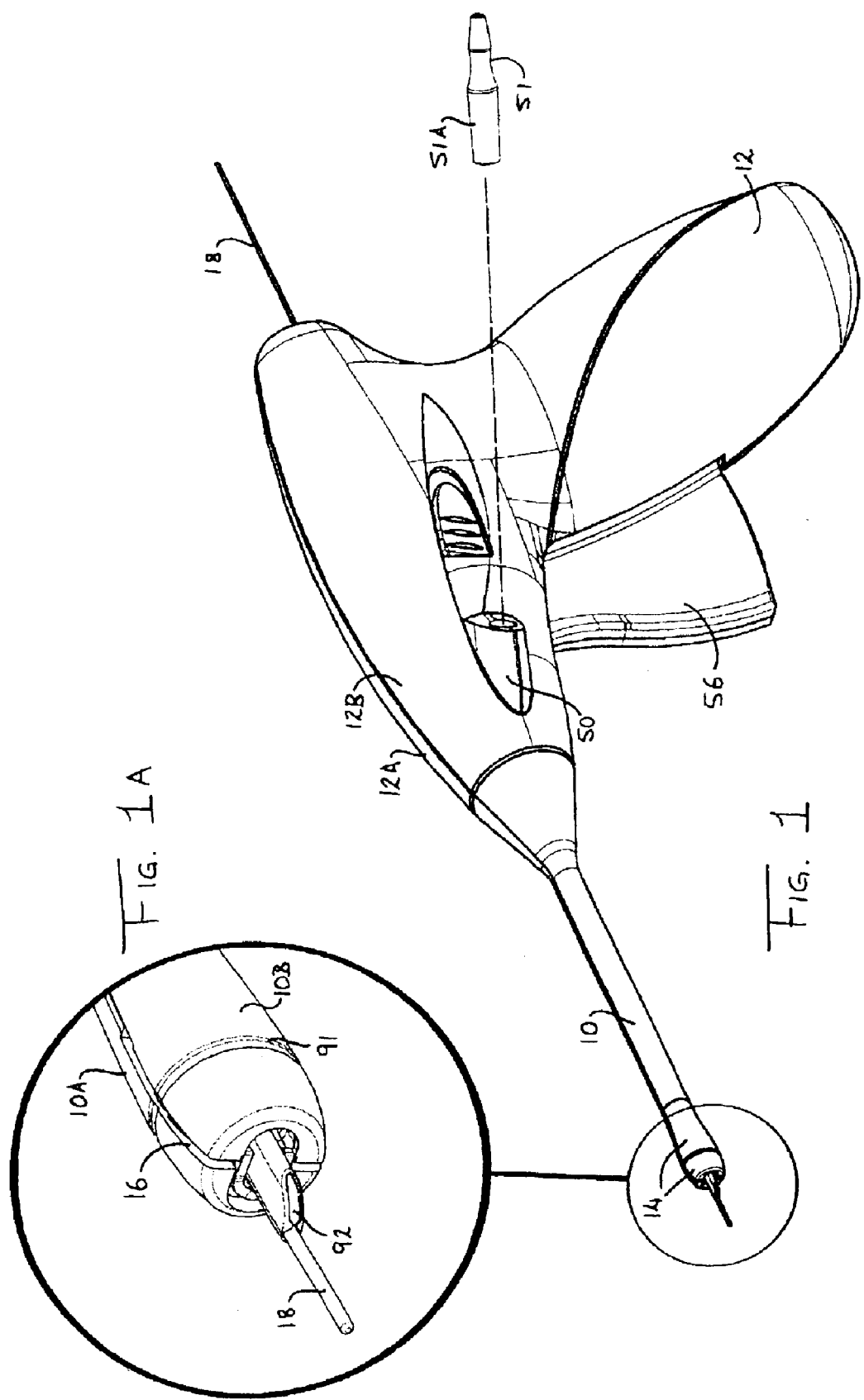
FIG. 1 is a perspective view of an embodiment of a surgical stapler according to the invention.

The purpose of the blood locator tube 92 is to follow a previously placed guidewire 18 to a puncture site in a blood vessel, thereby to locate the free end of bullet portion 14 of the shaft 10 against the exterior wall of the blood vessel at the puncture site. To properly locate the bullet portion 14 the front end of the tube 92 must actually penetrate the blood vessel wall at the puncture site and this is indicated by blood flowing back through the tube 92 and out through a blood outlet port 93 (FIG. 11) in the tube. A channel (not shown) in the part of the left-hand side 10B of the shaft 10 within the housing 12 provides communication between the port 93 and a blood exit port 50 (FIG. 1) on the side of the housing 12B, so that the blood flowing back through the tube 92 is visible at the exterior of the housing.

A blood exit port adapter 51 (FIG. 1) may be secured into the opening of the blood exit port 50 via a matching male luer taper 51A to enhance the visibility of the exiting blood. The blood exit port adapter has a reduced internal diameter, relative to the opening of the blood exit port 50, which for a constant blood flow increases the pressure of exiting blood causing a jet effect of exiting blood.

In the absence of the blood exit port adapter, the blood exit port's female luer taper opening matches that of the standard medical syringe's male luer taper making it possible at any time during the device's use to inject fluid via the blood exit port into the lumen of the locator tube to exit at its distal tip. This may be necessary from time to time to clear the locator tube's lumen of congealed blood and of trapped soft tissue. Alternatively, radiopaque contrast medium may be injected via the locator tube to confirm the relative location of the locator tube's distal tip to that of the blood vessel wall by fluoroscopy, or any injectable fluids may be injected for diagnostic or therapeutic reasons.

The blood outlet port 93 is sized to have a minimum area corresponding to the available blood entry area at the distal tip; however, is narrower (in a transverse aspect) than the diameter of the guidewire 18 to prevent the guidewire inadvertently exiting the blood outlet port during insertion, instead of exiting from the intended proximal end of the locator tube.

It has been found that the naturally formed shape of puncture wounds in arterial walls is elongated rather than round. Whereas the hole is formed by introducing instruments generally of round cross section, the wall tends to open generally along a transverse line which lies in the direction of the circumference of the artery (rather than along the axis of the artery). By having a generally oval blood locator tube, the locator tube (when introduced by the clinician with the major axis of the oval perpendicular to the axis of the artery), will fit more naturally within the arterial opening. The consequence of this is that the wound edges which are to be stapled together, lie closer together than if a tube of circular cross section were to be used.

This in turn has the consequence that the staple used need not be so large, and in turn, the dimensions of the shaft, which must accommodate the staple when in its unformed state, can be reduced, leading to less trauma for the tissue into and from which the shaft is introduced.

A further consequence of having a generally oval or elongated cross section for the locator tube is that the tube will be more disposed to the centre of the puncture than with a rounded tube. The present embodiment has a staple which straddles the locator tube, thereby increasing the likelihood of the staple closing the elongated wound at its centre rather than towards one or other of the extremities of the wound.

The opening 96 at the front of the tube 92 has an approximately circular portion 96A at the extreme forward tip of the tube which is of greater diameter than the width of the remaining portion 96B of the opening 96. The portion 96B is in the form of a slot which is aligned with the major axis of the elongated cross-section of the tube 92 and slopes rearwardly from the circular portion 96A. The guidewire 18, which passes through the tube 92, FIG. 11, is chosen to be of sufficiently smaller diameter than the diameter of the opening 96A at the front end of the tube 92 for the guidewire 18 to be easily inserted into the tube 92 and pass through the opening 96A. However, the guidewire is also chosen to be too large to fit within the remainder 96B of the opening 96. In this way guidewire 18 is constrained to remain in opening 96A, and the size of opening 96A sets an upper limit on the diameter of guidewire which can be used with the device. One could introduce a narrow neck or constriction into the opening 96 just above opening 96A (at the points indicated by 96C) to ensure that very small guidewires were constrained within the enlarged opening 96A, but in general this is unnecessary as the guidewire will normally be supplied with the device, or the device will only be supplied for use with a particular gauge of guidewire.

The rear crimp 94 and tip opening 96A are positioned to encourage the guidewire to lie along the bottom curved surface of the tube, i.e. that portion of the tube lying in a direct line between the opening in the crimped end and the opening 96A. This helps prevent guidewire 18 from laying up against the inside of blood exit port 93 and preventing egress of blood, FIGS. 11A and 11B.

The curvilinear nature of opening 96 increases the available inlet area to match that of the available area within the body of the locator tube with the guidewire 18 in situ.

The slot-like opening 96B slopes away from the circular opening 96A for ease of insertion into the vessel opening and to reduce the potential of trauma to the inner wall of the vessel opposite the opening being stapled. This is achieved because the guidewire 18 protruding from opening 96A will tend to push the opposite wall of the vessel away from the locator tube tip, and the point at which the guidewire protrudes (due to it being constrained in the opening 96A) is the farthest part forward of the tip. Thus, the shape of the tip is streamlined away from opening 96A to prevent any part of the tip gouging into or otherwise damaging the inner vessel walls. Also, the peripheral edges 95 of the opening 96 are bent inwardly to as to avoid sharp edges which might damage soft tissue and the vessel wall.

The distal end of an alternative embodiment of a locator tube 42 is shown in FIGS. 12 and 13. This embodiment also has a substantially constant elongated cross-section, which in this case converges to an approximately circular guidewire opening 46 at the extreme forward tip of the tube. The guidewire 18, which passes through the tube 42, is usually chosen to be of sufficiently smaller diameter than the diameter of the opening 46 for there to be an adequate gap for the blood to pass back through the tube 42 even in the presence of the guidewire. However, further openings 46A are provided in opposite sides of the tube 42 just behind the front opening 46 to allow more ready access of the blood to the interior of the tube in cases where the guidewire 18 may not leave a large enough gap for passage of blood solely through the opening 46. The three openings 46, 46A, 46A in fact form respective portions of a single front opening, being in reality three connected lobes, all connected by constricted channels 47, and all in communication with the interior of the tube.

Figure 13A:
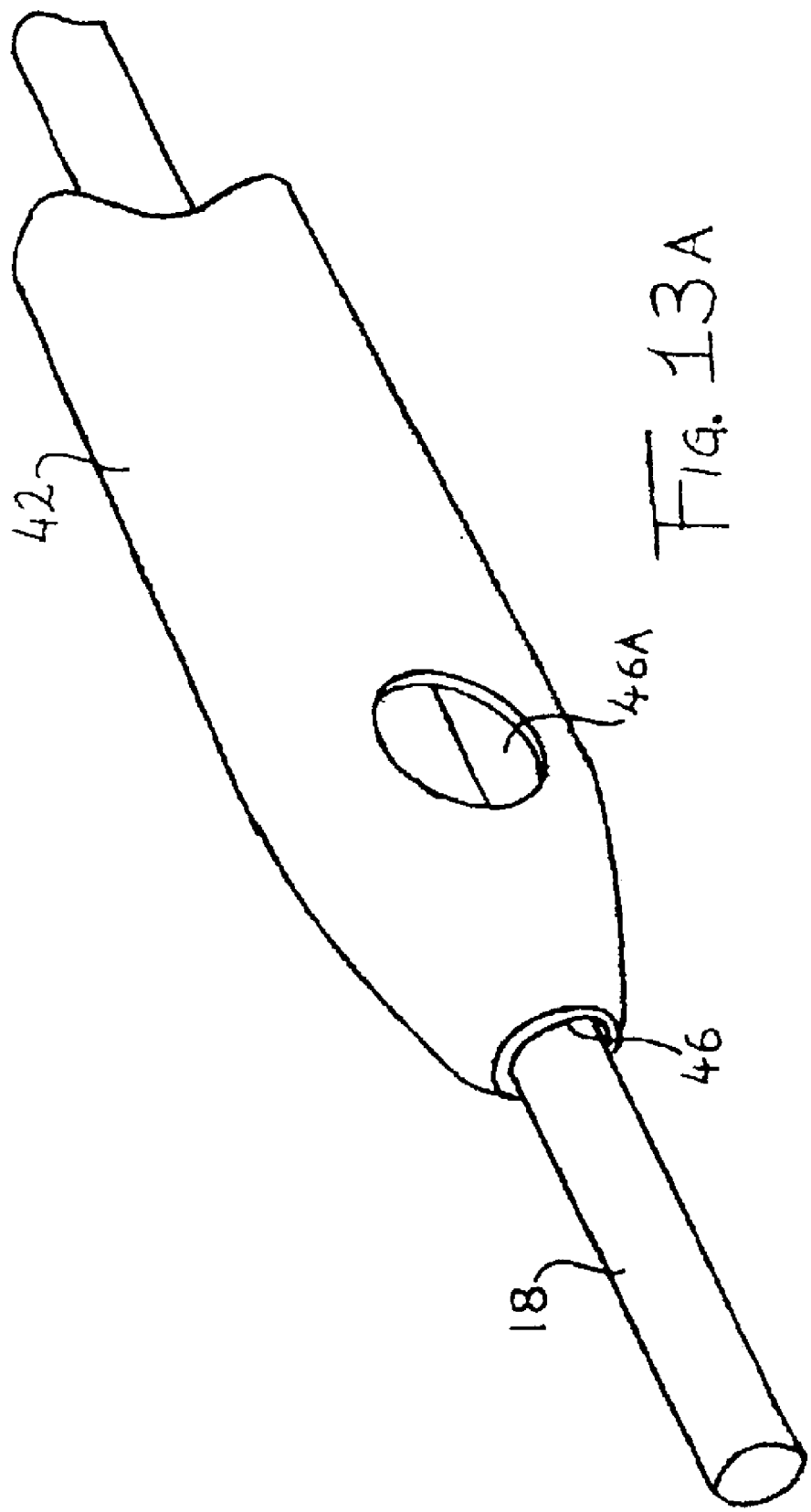
FIG. 13(A) is a perspective view of the front portion of an alternative embodiment of the blood locator tube shown in FIG. 12.

An alternative embodiment is shown in FIG. 13(A) where the three openings 46, 46A and 46A, while collectively constituting the front opening of the tube 42, are independent of each other. Again, opening 46 at the front of the tube is sized to receive a maximum size of guidewire and openings 46A are sized to allow a sufficient flow of blood to enter the locator tube.

A problem can arise in devices of this type where an oversized guidewire is used which occludes the hollow interior of the blood locator tube and thereby prevents blood flow back through the tube. To prevent this situation the lobe 46 through which the guidewire emerges in the tip of the tube of FIGS. 12, 13 and 13A is of a lesser diameter than the internal bore of the tube. The dimensions of this lobe 46 set a maximum for the guidewire diameter for use with the device, and ensure that even when this maximum diameter guidewire is used, there is still sufficient internal clearance within the tube bore to allow a strong blood flow through the tube from the other lobes 46A.

Figure 8:
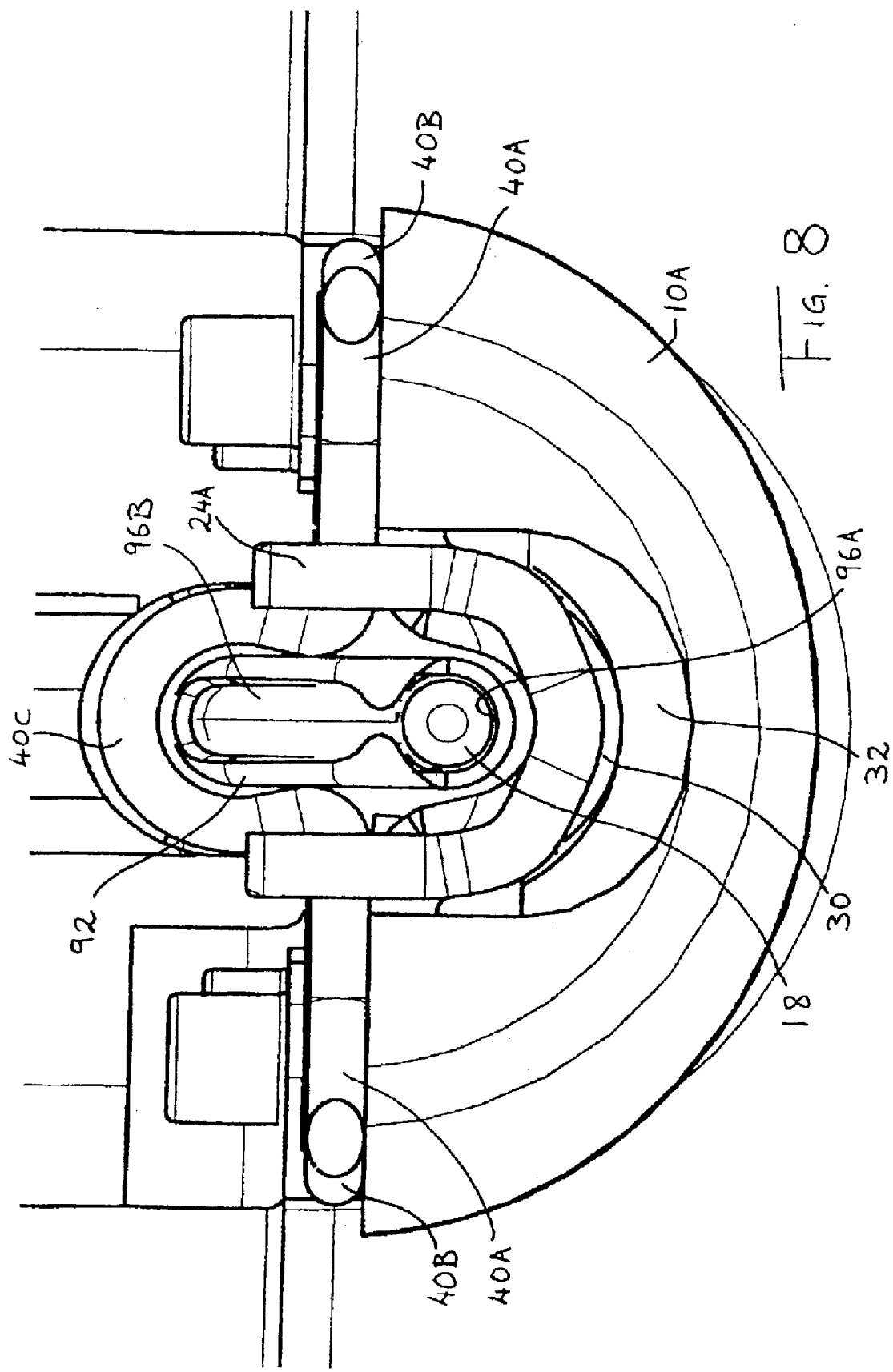
FIG. 8 is a front elevation of the components of FIG. 6 in the pre-fire position.

The staple 40 straddles the blood locator tube 92 within the bullet portion 14 of the shaft 10, see FIGS. 6 and 8, and is slidable thereon forwardly towards the free end of the bullet portion 14. In particular (see also the enlarged view of FIG. 14), the staple 40 comprises a back or base portion 40A from which extend perpendicularly at each end respective legs 40B which terminate in sharpened points. The base portion 40A and legs 40B lie in substantially a common plane except for a centre portion 40C of the base portion 40A which is deformed in a direction perpendicular to the legs 40B so as to have an Ω (omega) shape generally complementary to the external cross-sectional profile of the blood locator tube 92 and internal cross-section of an insert 160, to be described. The base section 40A is pre-bent to between 150° and 170° at points A and B equidistant from the centre of the base, positioned to maximise the closure of the closed staple (and is relevant to the depth of forming wings 54 on the former 52). The base section is also deformed at points C & D so as to narrow the cross sectional width of the wire at both points thereby directing the staple to bend at these points. The staple 40 is mounted on the blood locator tube 92 such that the centre portion 40C of the staple sits on the upper half of the tube 92, as seen in FIGS. 6 and 8, where the narrow open section of the omega shape is approximately equal to the width of the tube and with the legs 40B pointing forwardly on opposite sides of the tube 92. The depth of the centre portion 40C of the staple 40 is such that the legs 40B of the staple lie substantially directly on opposite sides of the central axis of the tube 92. This will ensure that the staple 40 is positioned centrally across the puncture hole in the blood vessel. In order to avoid the guidewire 18 fouling the staple 40 when the latter is closed on the puncture site, the hole 96A is offset below the plane containing the legs 40B of the staple, FIG. 8.

Figure 18:
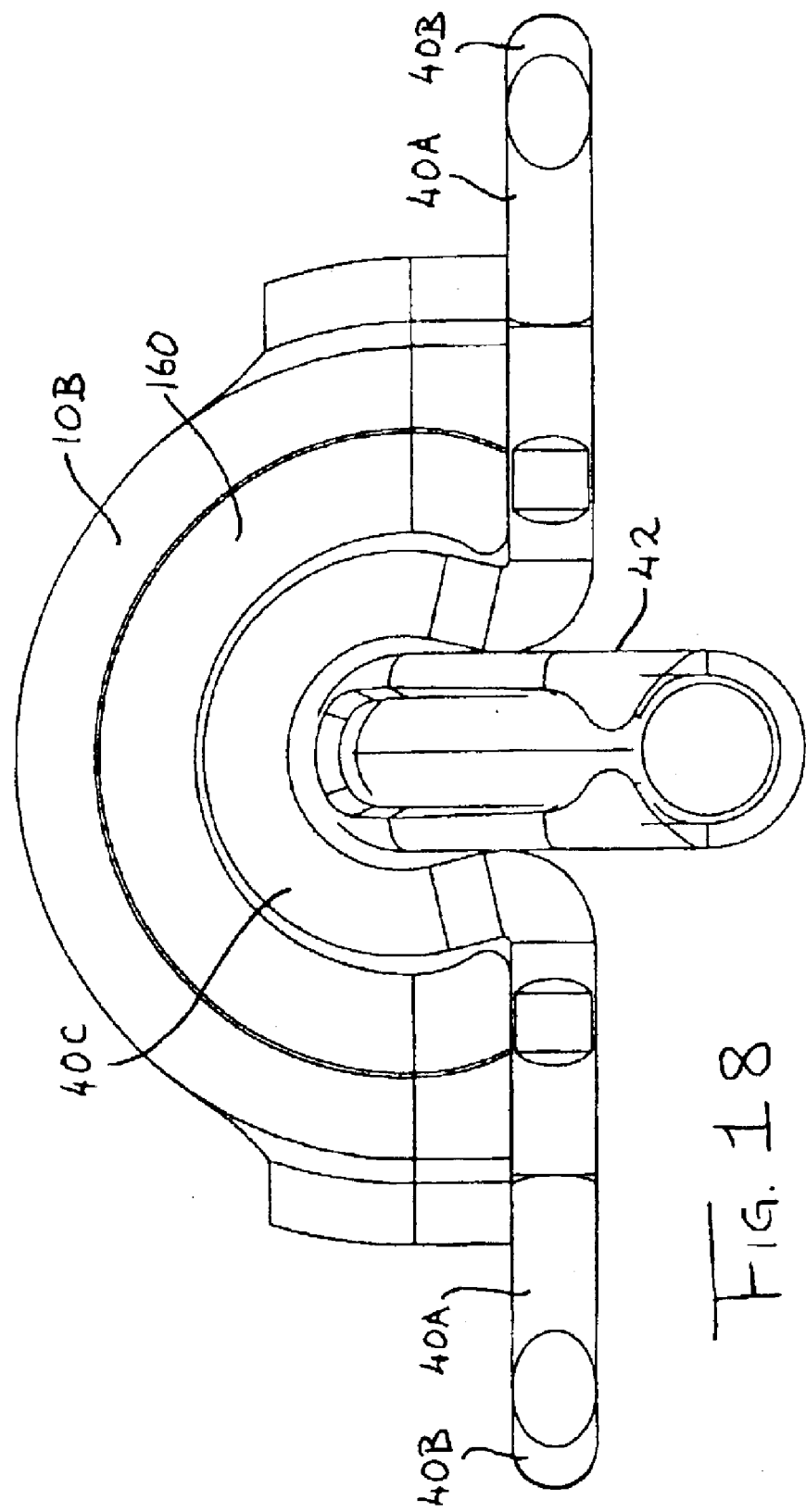
FIG. 18 is an end view of the surgical staple, locator tube and insert.

The metal insert 160 is received in a recess in the left-hand shaft side 10B within the bullet section 14. The insert 160 provides mechanical support for the omega section 40C of the staple 40 during the staple forming process and is engaged by the former 52 during the staple ejection phase of the process so as to separate both halves of the bullet section for easy staple release. The insert is profiled to generally correspond with the external profile of the omega shaped portion 40C of the staple. At the distal end the insert profile tapers down to closely approximate the omega-shaped portion of the staple 40C (FIG. 18). This has the effect of offering mechanical support to the omega-shaped portion of the staple during the staple forming process, during which the base section is bent about the anvil fingers. This bending motion in turn causes the omega to open up or flatten out. The metal insert prevents this from happening only allowing the staple base to deform around the anvil. The omega interlock system between the staple 40 and insert 160 (FIG. 18) also stabilises the staple, vertically, within the staple exit plain during the forming process, whilst allowing easy staple release once formed, due to the relatively small contact area between staple and insert.

The staple former 52 has a cross-section conforming to that of the blood locator tube 92 and is slidable on the blood locator tube 92 axially within the shaft 10. The former 52 is located behind the staple 40 on the tube 92 and is operated by the cam mechanism 62. At its front end the former 52 has a pair of forming arms 54 which are so shaped that, when the former 52 is driven forward by the cam mechanism 62, the staple 40 is driven against and deformed around the anvil fingers 24A so that the legs 40B of the staple close together (FIG. 9) onto the puncture site. The surface of the forming arms which contact the staple 55 may be so profiled to match the cross-sectional geometry of the staple. This matching profile stabilises the staple on the forming surfaces of the forming arms 54 during the high pressure contact with the staple during staple forming and closure. During the forward movement of the staple, the staple legs slide toward the anvil 24 along a track defined by the staple exit slot 16 between the opposite halves the bullet portion 14. The slot 16 provides a slight interference fit on the staple legs 40B to prevent the staple 40 moving forward during storage of the device or prior to firing. The slot 16 further prevents the staple rotating in the horizontal plane (FIGS. 7 and 10) during its forward travel. Once forming of the staple around the anvil is completed the forming force is removed from the former 52 by a drop-off in the cam, the anvil is lowered and the former advanced again to eject the staple from the device. During this forward movement (ejection phase), the sloped edges 52A and 52B of the former engage with the metal insert 160 to prise open the bullet section of the shaft assembly thus facilitating staple release.

Figure 3:
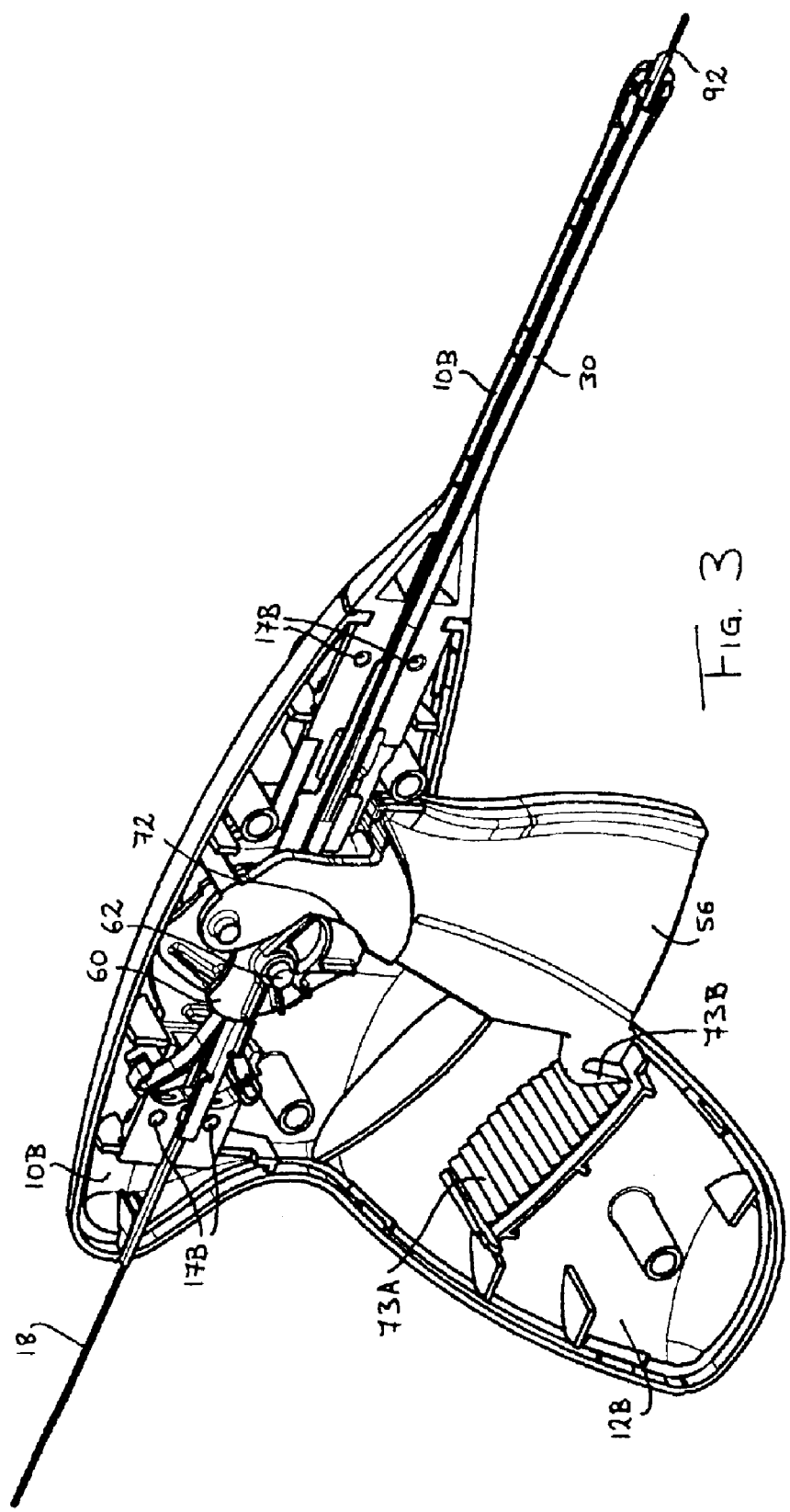
FIG. 3 is a perspective view of the stapler of FIG. 1 with the right-hand side handle and shaft removed.
Figure 16:
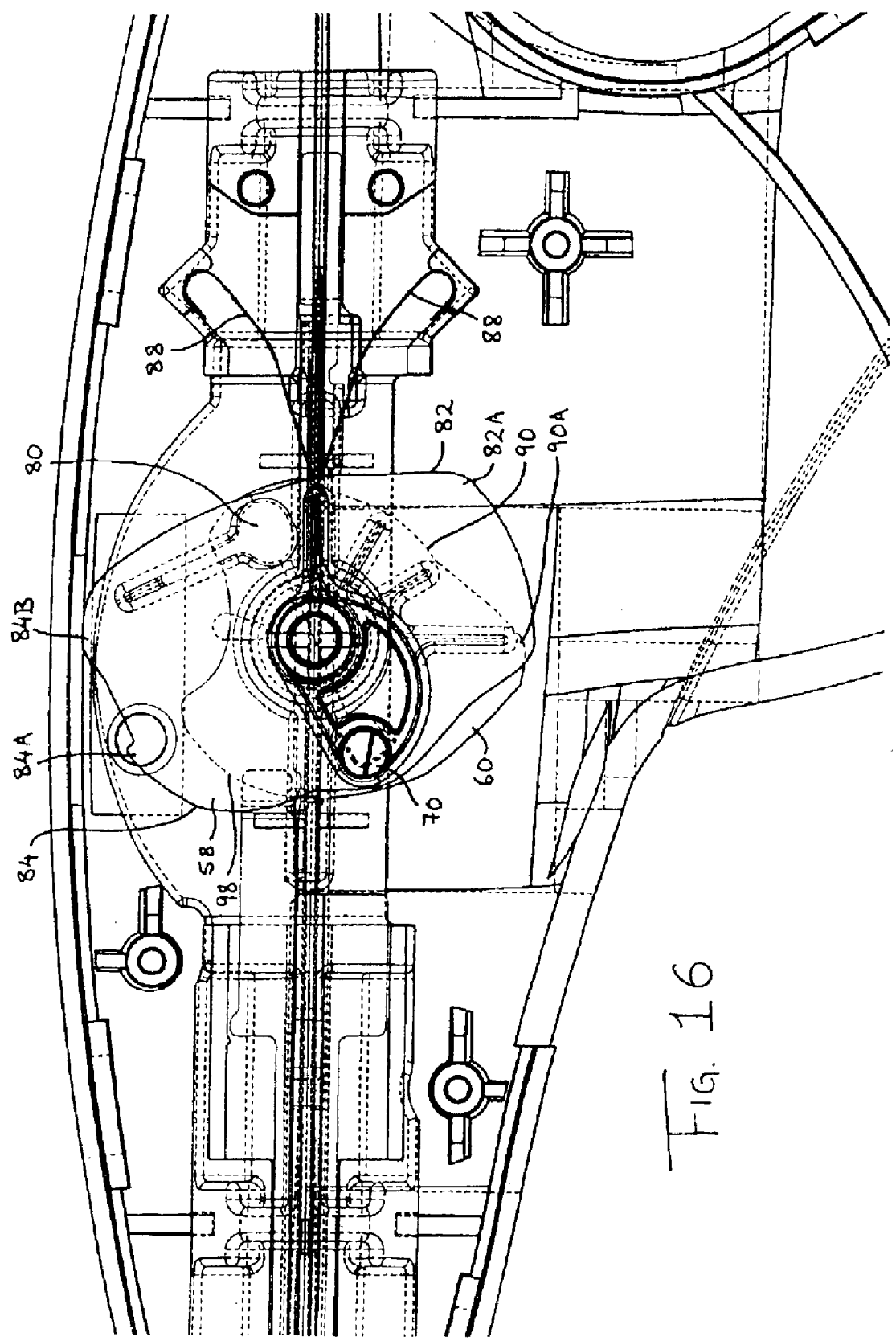
FIG. 16 is a side elevation of the cam mechanism.

The cam mechanism 62 can be seen in FIG. 3 and in enlarged views of FIGS. 15 and 16. The mechanism 62 consists of a first cam 58 and a second cam 60 mounted on a common axis 62 which sits in a recess 64 in the left-hand side 10A of the shaft (FIG. 4) and a corresponding recess (not shown) in the right-hand side 10B. Trigger 56 is similarly mounted in the shaft by a pair of stub axles 66 which are received in a trigger seating recess 68 in each half of the shaft 10, FIG. 4.

An actuating pin 70 extends through the first and second cams 58, 60. This actuating pin is acted on by a cam actuating surface 72 (FIG. 3) provided on the trigger 56, so that when the trigger is squeezed the actuating surface moves the actuating pin in an anticlockwise direction around the axis 62. Because the actuating pin extends through both cams 58, 60 of the mechanism 62, the cams are both rotated simultaneously through the same angle as determined by the trigger squeeze. The use of this cam mechanism ensures accurate timing and positive mechanical displacements of all the moving components and accurate movement of the components relative to each other. The geometry of the trigger pivot pins 66 and actuating surface 72 relative to the cam pivot 62 and cam actuating pin 70 is configured to minimise the trigger rotation to only 23 degrees whilst the cam rotates a total of 90 degrees. This configuration also provides a mechanical advantage that the trigger delivers to the cam-actuating pin 70 of approximately 1:4. This geometry is further configured to deliver the best mechanical advantage at the phase during the staple forming cycle, which requires the highest forming forces, having the advantage of minimising the trigger effort and ensuring a constant trigger effort over the full cycle. Trigger 56 further comprises a ratchet lever 73B, shown in FIG. 3, which engages with ratchet strip 73A, which is mounted in the right handle 12A, FIG. 3. This non-return ratchet system ensures the firing cycle of the staple is uninterrupted, non-repeatable and provides a positive indication that the device has been used.

Referring back to FIG. 3, a leaf spring 88 positioned in a recess in the left-hand side 10A of the shaft and a corresponding recess (not shown) in the right-hand side 10B. The free ends of the spring are formed into a loop so as to pivot freely in the curved corner recesses in which it sits and to aid assembly. The apex of this spring is positioned in a slot 74 in the crimped portion 94 of the blood locator tube 92 thus assuming the role of cam follower for the blood locator tube. This blood locator tube cam follower 74 is acted on by the first cam 58. Similarly, the first cam 58 acts on a former cam follower 76, whereas the second cam 60 acts on anvil-support cam followers 78A and 78B. The shape of the first and second cams 58, 60 are shown in elevation in FIG. 16 (the second cam 60 is shown in dotted outline as it is concealed by the first cam). FIG. 16 also shows actuating pin 70, and a reinforcing strut 80 mounted between the first and second cams diametrically opposite the actuating pin 70.

The cams are shown in the starting positions in FIGS. 15 and 16. Squeezing the trigger fully (through an angle of 23 degrees) causes the cams to rotate anticlockwise through 90 degrees.

The apex of the leaf spring 88 which engages with and operates as a cam follower for the blood locator tube (leaf spring apex) acts against the rear surface 82 of the first cam 58. As the first cam rotates anticlockwise from the position shown in FIG. 15, the distance between the blood locator tube cam follower 74 and the axis 62 is increased. This causes the blood locator tube to be drawn backwards as the trigger is squeezed.

The former cam follower 76 acts against the front surface 84 of the first cam 58. Again the distance between former cam follower 76 and axis 62 increases through the initial stages of the trigger being squeezed. The profile of surface 84 is designed with two distinct non-linear efficiencies, transitioned from low mechanical efficiency/high displacement to high mechanical efficiency/low displacement. The first rise rate being for displacement of the staple from its starting position to initial forming against the anvil, which requires the largest displacement of the staple with minimal load. The second non-linear rise rate is designed to correlate the cams mechanical efficiency with the load profile required to form the closed staple, minimising the trigger effort required and ensuring a constant trigger effort over the full cycle. A V-shaped section 84A of front section 84 causes the former 52 to momentarily suspend its forward motion when the staple has been fully formed. The effect of this is to momentarily release the pressure off the formed staple against the anvil, allowing the anvil to be dropped. The geometry of the distal tip of the former is designed to provide sufficient intrinsic spring tension to allow the forming arms 54 to further squeeze the formed staple, once the anvil has dropped, to further closed the formed staple. As the cam continues to rotate the raised profile 84B on the cam causes the former to advance forward again, ejecting the staple clear of the device.

It can be seen that a raised hump 82A on the profile of the rear surface 82 of the first cam is located almost diametrically opposite the V-shaped section 84A. The reason for this is to increase the rate at which the blood locator tube is drawn out of the puncture site just before the staple is fully formed and released. The intention is to leave the tube in the puncture as late as possible to provide support for the walls of the blood vessel for as long as possible And also to ensure that the head of the device remains centred over the puncture hole. The blood locator tube 92 is biased forward by the blood locator tube leaf spring 88 which also maintains pressure between the apex of the spring and the rear surface 82 of the first cam 58.

The blood locator tube leaf spring 88 allows the locator tube to be displaced in a proximal direction (back into the shaft of the device) against the spring tension in the event that the locator tube meets any significant resistance during insertion of the device, to prevent unnecessary trauma to soft tissues, the vessel or its rear wall.

An example of where this is particularly useful is if the stapler is advanced too far into the vessel, so that the tip of the tube 92 meets the inner wall. The blood locator tube will then be displaced back into the shaft, and may be designed to protrude through the end of the handle housing to give a visual indication that the device has been inserted against the wall. Furthermore, the device may be designed so that the blood outlet port 93 on the tube 92 is brought out of registry with the blood exit port 50 in the handle housing when the tube is displaced backwards, so that the clinician will note the flow of blood ceasing when the tube meets the inner vessel wall in this way.

The cam mechanism 62, however, provides positive mechanical displacements for withdrawing the locator tube at the appropriate timing, to ensure there is no chance of the staple being formed whilst the locator tube is in a forward position and potentially interfering with the staple formation.

A further reason to leave the blood locator tube in the puncture hole as late as possible is that the continued retraction of the tube everts or turns outwards the opposed edges of the puncture wound and aids penetration of the staple legs into the arterial wall. Eversion of the edges of the puncture helps prevent thrombus formation within the vessel. Yet another reason to leave the blood locator tube in the puncture hole as late as possible is to ensure that the stapler head remains centred over the hole during the staple delivery process. When the locator tube is fully retracted, only the guidewire is left within the wound, and this will be easily retracted from the closed wound after the stapler has been removed from the puncture site.

The anvil-support cam follower 78B acts against the rear surface 90 of the second cam 60. It can be seen that this rear surface 90 provides the greatest increase in distance relative to the axis to the section 90A from about 60 to 90 degrees below the horizontal. The reason for this is that the anvil is maintained in place until the staple has been formed and the pressure on the former has been relaxed slightly to allow the anvil to drop. The anvil is maintained in place for the initial 60 degrees of rotation by the anvil-support cam follower 78A being in contact with cam surface 98 of cam 60, preventing the anvil-support 30 from moving from its starting position. The cam surface 98 for the first 60 degrees of cam rotation is at a constant distance from the cam axle 62 (in dwell).

In use, the stapler is initially in the "pre-fire" configuration shown in FIGS. 6 to 8. The front end of the blood locator tube 92 is in a fully forward position projecting beyond the free end of the bullet portion 14 of the shaft 10, the anvil-support 30 is in a fully forward position with its arms 36 extending under the anvil's support wings 25 ensuring the anvil fingers 24A are directly in front of the staple 40, the former 52 is in a fully retracted position away from the anvil fingers 24A, and the staple 40 is in its fully back position up against the forming arms 54.

In this configuration the external end of a previously positioned guidewire 18 is inserted into the hole 96A in the front end of the blood locator tube 92 and fed through the tube 92 until it exits a guidewire exit port at the rear of the housing 12. The stapler is now fed along the guidewire 18 until the tip 95 of the tube 92 enters the blood vessel lumen through the vessel's puncture hole. This is indicated by blood flowing out of the blood exit port 50 or, if present, the adapter 51. At this point the front end of the bullet portion 14 of the shaft 10 will be resting against the exterior wall of the blood vessel.

Now the trigger 56 is squeezed, causing the cams of the cam mechanism 62 to rotate through 90 degrees. As mentioned, the rear end of each of the blood locator tube 92, anvil-support 30 and former 52 are coupled to the cam mechanism via cam followers and the following coordinated movement of these components takes place as the cams rotate through 90 degrees.

(A).

0 degrees: Stapler in pre-fire configuration.

32 degrees: Former 52 forward sufficiently to clamp staple against anvil fingers 24A, blood locator tube begins to retract. At this point the staple legs will have punctured the wall of blood vessel, but the staple is not yet fully deformed.

50 degrees: Former 52 forward sufficiently to deform the staple legs around the anvil fingers 24A and close the staple on the puncture site: blood locator tube 42 fully retracted. At some point between 32 and 50 degrees, the blood locator tube will have withdrawn from between the staple legs in time to allow them to close. This should be left as late as possible to provide support for the walls of the blood vessel for as long as possible.

65 degrees: Clamp force released from staple (due to drop off in cam profile). Anvil support 30 starting to retract.

75 degrees: Anvil support 30 retracted sufficiently to act against anvil sloped tilt arms 24B. Anvil fingers 24A begin to drop.

83 degrees: Anvil support 30 fully retracted. Anvil fingers 24A dropped down to allow release of staple. Intrinsic tension in former arms 54 further closes the staple. Former 52 begins to move forward again to eject staple. Former 52 begins to interfere with the insert 160 to spread bullet portion 14 of the shaft to allow for clear staple release.

90 degrees: Former 52 fully forward; staple ejected from the device.

The use of cams in cam mechanism 62 ensures the accuracy of sequence and relative timing between events as well as ensuring positive mechanical displacements of all components.

In a further embodiment to the above described device, on the completion of the cycle described above, further rotation of the cam causes the anvil support 30 to return to its fully forward position, lifting the anvil fingers 24A to their raised position behind the formed staple being held in forming arms 54. The former is then retracted in a proximal direction (back into the shaft) causing the rear of the closed staple to crash into the raised anvil fingers 24A, to be positively ejected from within the forming arms 54 and the device. The additional movements of the anvil support and former may be facilitated by additional cam lobes on cam 58; or alternatively spring driven, assisted and timed by appropriately positioned radial slots in cam 58 to allowing the cam follower of the anvil support to move forward and the cam follower of the former to move rearwards.

In a further embodiment the trigger activates an automatic firing cycle, not shown. A tension spring attached to the cams is released from its extended state so as to rotate the actuation cam through a 90 degree arc causing the same component movements as described above.

In an alternative embodiment, not shown, once the staple has been formed the forward end of the former 52 retracts and engages pull arms on the anvil-support 30 causing it to move in a rearward direction. As it does so, it engages with the rear end of the anvil 24, which is angled downward into the path of the moving slide. Centrally opposed wings extend from the anvil and are located so as to pivot in opposed wing slots formed in the right-hand side 10A of the shaft. Once engaged with the slide the rear end of the anvil is pushed upward causing it to pivot about the wings and arc the forward end of the anvil downward. As it does so, it disengages from the staple so that the device can be removed from the puncture tract along the guidewire.

In a further embodiment the reverse profile 82 on the first cam 58 which engages with the cam follower 74 on the blood locator tube 92 is extended so that when the staple forming cycle is completed the first cam continues to rotate causing the blood locator tube to move further in a proximal direction. At its distal end the blood locator tube has wings which as it moves in a proximal direction engages with the pull arms of the anvil-support 30 causing it to move in a proximal direction and engage the anvil tilt arms thereby disengaging the distal end of the anvil from the formed staple. In this embodiment the second cam is redundant and can be omitted.

In a further embodiment, FIG. 17, the bullet head 14 of the shaft 10, which approximates the blood vessel wall 208, includes a number of suction ports 200. These ports are in communication with a suction adapter 202 via capillaries 204 within the shaft section. Suction, from a standard wall suction outlet or independent suction pump, is supplied to the suction adapter 202 via an on/off tap 206. Once the device is in position on the arterial wall, as indicated by blood flowing from the blood exit port, the tap 206 is turned to the "on" position thereby delivering suction to the ports 200 on the bullet head 14. This in turn suctions the blood vessel wall 208 against the face of the head 14 so as to stabilise it during delivery of the staple. Once delivered the suction is deactivated so as to remove the device from the blood vessel wall and tissue tract.

The invention is not limited to the embodiments described herein and may be modified or varied without departing from the scope of the invention.

What is claimed is:

1. A surgical stapler comprising:
   a shaft;
   a locator slidably movable with respect to the shaft between a forward position in which the locator projects beyond a free end of the shaft to enter a puncture site in a liquid-carrying vessel and thereby locate the free end of the shaft at the puncture site, and a rearward position in which the locator is retracted relative to the shaft; and
   an actuator for driving a staple through the shaft and for simultaneously retracting the locator such that the locator is withdrawn from between legs of the staple in time to allow the legs of the staple to staple together opposite edges of the puncture site.

2. The surgical stapler of claim 1, further comprising an anvil against which a staple may be deformed to staple together opposite edges of a puncture site.

3. The surgical stapler of claim 2, wherein the anvil is tiltable relative to an axis of the shaft between a first position in which the anvil is in a position for engagement by a staple, and a second position in which the anvil is clear of the staple.

4. The surgical stapler of claim 3, wherein the actuator further includes a tilting mechanism for tilting the anvil in coordination with the movement of the locator and staple such that the anvil is tilted from the first position to the second position after closure of the staple onto a puncture site.

5. The surgical stapler of claim 4, wherein the tilting mechanism for tilting the anvil comprises an elongated member slidable axially within the shaft.

6. The surgical stapler of claim 1, further comprising a staple having forwardly pointing legs disposed respectively on opposite sides of the locator.

7. The surgical stapler of claim 6, wherein the actuator drives the staple via an elongated former slidable axially of the shaft.

8. The surgical stapler of claim 1, wherein the locator comprises a hollow tube having an opening at the forward end to enable liquid flow to be sensed within a liquid-carrying vessel to thereby locate the puncture site in the vessel.

9. The surgical stapler of claim 8, wherein the locator tube is adapted to slidably receive a guidewire.

10. The surgical stapler of claim 1, wherein the locator comprises a hollow tube having an opening at the forward end to enable a radiopaque liquid to be injected through the tube to thereby locate the puncture site in the vessel by fluoroscopy.

11. A surgical instrument for closing a puncture in a liquid-carrying vessel, comprising:

a shaft;

a locator slidably movable with respect to the shaft between a forward position in which the locator projects beyond a free end of the shaft to enter a puncture site in a liquid-carrying vessel, and a rearward position in which the locator is retracted relative to the shaft; and an actuator for driving a closure device toward the puncture site and for simultaneously retracting the locator such that the locator is withdrawn from the closure device to allow the closure device to close the puncture.

12. The surgical instrument of claim 11, further comprising a closure device disposed around the locator and having at least two tissue-penetrating legs formed thereon.

13. The surgical instrument of claim 12, wherein the at least two tissue-penetrating legs of the closure device are movable between a first, pre-deployed position, wherein the legs are substantially parallel to one another, and a second, deployed position wherein the legs extend toward one another.

14. The surgical instrument of claim 11, wherein the closure device is a staple.

15. The surgical instrument of claim 11, wherein the closure device includes at least two legs that extend forwardly on opposite sides of the locator before the locator is retracted.

16. The surgical instrument of claim 11, wherein the locator comprises a hollow tube having an opening at a forward end and an open at a rearward.

17. The surgical instrument of claim 11, wherein the locator comprises a hollow tube having an opening at the forward end to enable liquid flow to be sensed within a liquid-carrying vessel to thereby locate the puncture site in the vessel.

18. The surgical instrument of claim 11, wherein the locator comprises a hollow tube having an opening at the forward end to enable a radiopaque liquid to be injected through the tube to thereby locate the puncture site in the vessel by fluoroscopy.

19. The surgical instrument of claim 11, wherein the locator is adapted to slidably receive a guidewire.

20. A surgical instrument for closing a puncture in a liquid-carrying vessel, comprising:

a shaft having a tube slidably disposed therein, the tube being adapted to extend forward of the shaft to be positioned through a puncture in a liquid-carrying vessel; and an actuator mechanism adapted to simultaneously retract the tube from the puncture in the liquid-carrying vessel while delivering a closure device to close the puncture.

21. The surgical instrument of claim 20, further comprising a closure device disposed around the tube and having at least two tissue-penetrating legs formed thereon.

22. The surgical instrument of claim 21, wherein the at least two tissue-penetrating legs of the closure device are movable between a first, pre-deployed position, wherein the legs are substantially parallel to one another, and a second, deployed position wherein the legs extend toward one another.

23. The surgical instrument of claim 20, wherein the closure device is a staple.

24. The surgical instrument of claim 20, wherein the closure device includes at least two legs that extend forwardly on opposite sides of the tube before the tube is retracted.

25. The surgical instrument of claim 20, wherein the tube comprises a hollow tube having an opening at the forward end to enable liquid flow to be sensed within a liquid-carrying vessel to thereby locate the puncture site in the vessel.

26. The surgical instrument of claim 20, wherein the locator comprises a hollow tube having an opening at the forward end to enable a radiopaque liquid to be injected through the tube to thereby locate the puncture site in the vessel by fluoroscopy.

27. The surgical instrument of claim 20, wherein the tube is adapted to slidably receive a guidewire.

28. A method for closing a puncture in a liquid-carrying vessel, comprising:

advancing a tube through a puncture in a liquid-carrying vessel;

positioning a shaft slidably disposed around the tube adjacent the puncture in the liquid-carrying vessel;

delivering a closure mechanism along the tube to the puncture in the liquid-carrying vessel; and activating an actuator mechanism effective to simultaneously separate the tube from the closure mechanism to allow the closure mechanism to close the puncture in the liquid-carrying vessel.

29. The method of claim 28, wherein the closure mechanism includes at least two tissue-penetrating legs formed thereon.

30. The method of claim 29, wherein the at least two tissue-penetrating legs of the closure mechanism are movable between a first, pre-deployed position, wherein the legs are substantially parallel to one another, and a second, deployed position wherein the legs extend toward one another.

31. The method of claim 28, wherein the closure mechanism is a staple.

32. The method of claim 28, wherein the closure mechanism includes at least two legs that extend forwardly on opposite sides of the tube before the tube is retracted.

33. The method of claim 28, wherein the tube comprises a hollow tube having an opening at a forward end, and wherein the step of advancing the tube through the puncture in the liquid-carrying vessel further comprises locating the puncture site in the vessel by sensing liquid flow through the opening at the forward end of the hollow tube.

34. The method of claim 28, wherein the tube comprises a hollow tube having an opening at a forward end, and wherein the step of advancing the tube through the puncture in the liquid-carrying vessel further comprises locating the puncture site in the vessel by injecting a radiopaque contrast medium through the hollow tube and confirming the relative location of the tube by fluoroscopy.

35. The method of claim 28, wherein the tube is adapted to slidably receive a guidewire.

36. A surgical stapling apparatus comprising:

a hollow shaft;

a member slidably receivable within the hollow shaft and movable between a forward position in which the member projects beyond a forward end of the hollow shaft to position the forward end of the hollow shaft over a puncture in a liquid-carrying vessel, and a rearward position in which the member is retracted relative to the hollow shaft; and an actuator for driving a staple through the hollow shaft to staple together the puncture and for simultaneously retracting the member as the staple is released.

37. The surgical stapling apparatus of claim 36, wherein the member comprises a blood locator tube.

38. The surgical stapling apparatus of claim 36, wherein the member is adapted to be positioned between legs of a staple when the member is in the forward position.

39. The surgical stapling apparatus of claim 36, wherein the member is adapted to extend into a puncture in a liquid-carrying vessel when the member is in the forward position.

40. The surgical stapling apparatus of claim 36, further comprising a guide wire adapted to slidably receive the surgical stapling apparatus to guide the surgical stapling apparatus to the puncture.

41. The surgical stapling apparatus of claim 36, wherein the actuator comprises a movable trigger.

42. The surgical stapling apparatus of claim 41, wherein the movable trigger is coupled to a housing formed on a proximal end of the hollow shaft.

43. The surgical stapling apparatus of claim 36, wherein the member is adapted to be positioned in alignment with a staple when the member is in the forward position.

* * * * *